US010570186B2

(12) United States Patent
Cooper et al.

(10) Patent No.: US 10,570,186 B2
(45) Date of Patent: Feb. 25, 2020

(54) CHIMERIC ANTIGEN RECEPTORS (CAR) TO SELECTIVELY TARGET PROTEIN COMPLEXES

(71) Applicant: BOARD OF REGENTS, THE UNIVERSITY OF TEXAS SYSTEM, Austin, TX (US)

(72) Inventors: Laurence J. N. Cooper, Houston, TX (US); Bipulendu Jena, Houston, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 63 days.

(21) Appl. No.: 15/524,321

(22) PCT Filed: Nov. 4, 2015

(86) PCT No.: PCT/US2015/059072
§ 371 (c)(1),
(2) Date: May 4, 2017

(87) PCT Pub. No.: WO2016/073629
PCT Pub. Date: May 12, 2016

(65) Prior Publication Data
US 2017/0334968 A1   Nov. 23, 2017

Related U.S. Application Data

(60) Provisional application No. 62/075,627, filed on Nov. 5, 2014.

(51) Int. Cl.
| C07K 14/725 | (2006.01) |
| C07K 14/705 | (2006.01) |
| C07K 16/28 | (2006.01) |
| C07K 16/30 | (2006.01) |
| A61K 39/00 | (2006.01) |

(52) U.S. Cl.
CPC .... *C07K 14/7051* (2013.01); *C07K 14/70521* (2013.01); *C07K 14/70578* (2013.01); *C07K 16/2863* (2013.01); *C07K 16/30* (2013.01); *A61K 2039/505* (2013.01); *C07K 2317/32* (2013.01); *C07K 2317/526* (2013.01); *C07K 2317/622* (2013.01); *C07K 2317/73* (2013.01); *C07K 2319/00* (2013.01)

(58) Field of Classification Search
None
See application file for complete search history.

(56) References Cited

U.S. PATENT DOCUMENTS

| 4,690,915 A | 9/1987 | Rosenberg |
| 6,225,042 B1 | 5/2001 | Cai et al. |
| 6,355,479 B1 | 3/2002 | Webb et al. |
| 6,362,001 B1 | 3/2002 | Cai et al. |
| 6,410,319 B1 | 6/2002 | Raubitschek et al. |
| 6,790,662 B1 | 9/2004 | Leturcq |
| 7,109,304 B2 | 9/2006 | Hansen et al. |
| 2007/0032637 A1 | 2/2007 | Yokoyama |
| 2012/0121596 A1 | 5/2012 | Fuh et al. |
| 2013/0280220 A1 | 10/2013 | Nabil et al. |

FOREIGN PATENT DOCUMENTS

| WO | WO2017048902 | 3/1917 | |
| WO | WO2017075147 | 5/1917 | |
| WO | WO2007103009 | 9/2007 | |
| WO | WO2010108127 | 9/2010 | |
| WO | WO-2010108127 A1 * | 9/2010 | ......... C07K 16/2863 |
| WO | WO2013074916 | 5/2013 | |
| WO | WO2013084147 | 6/2013 | |
| WO | WO2014164554 | 10/2014 | |
| WO | WO2014186469 | 11/2014 | |
| WO | WO2014190273 | 11/2014 | |
| WO | WO2015061694 | 4/2015 | |
| WO | WO2015123642 | 8/2015 | |
| WO | WO2015164594 | 10/2015 | |
| WO | WO2015164740 | 10/2015 | |
| WO | WO2016073629 | 5/2016 | |
| WO | WO2016073755 | 5/2016 | |
| WO | WO2016138091 | 9/2016 | |
| WO | WO2016145146 | 9/2016 | |

OTHER PUBLICATIONS

Davies et al., Mol Med 18:565-76 (Year: 2012).*
Jena et al. (Blood, Aug. 19, 2010, 116 (7): 1035-1044) (Year: 2010).*
Almagro & Fransson, Frontiers in Bioscience 2008; 13:1619-33 (Year: 2008).*
Brentjens et al., CD19-Targeted T Cells Rapidly Induce Molecular Remissions in Adults with Chemotherapy-Refractory Acute Lymphoblastic Leukemia. Sci. Transl. Med., 5:177ra138, 2013.
Brentjens et al., Safety and persistence of adoptively transferred autologous CD19-targeted T cells in patients with relapsed or chemotherapy refractory B-cell leukemias. Blood, 118:4817-4828, 2011.
Cooper et al., Good T cells for bad B cells. Blood, 119:2700-2702, 2012.
Davies et al., "Flexible targeting of ErbB dimers that drive tumorigenesis by using genetically engineered T cells.", *Molecular Medicine*, 18(1):565-576, 2012.
Grupp et al., "Chimeric Antigen Receptor-Modified T Cells for Acute Lymphoid Leukemia", *New Eng. J. of Med.*, 18:1509-1518, 2013.
International Search Report and Written Opinion issued in International Application No. PCT/US2015/059072, dated Feb. 3, 2016.
Jena et al., "Specifically Targeting the Interface Between HER1-HER3 Heterodimer on Breast Cancer to Limit Off-Target Effects Using Chimeric Antigen Receptor Designs with Improved T-Cell Energy Balance", *Blood*, 124(21):2151, Dec. 1, 2014.

(Continued)

*Primary Examiner* — Peter J Reddig
(74) *Attorney, Agent, or Firm* — Parker Highlander PLLC

(57) ABSTRACT

Chimeric antigen receptor (CAR) constructs are provided that are able to selectively bind to specific protein complexes, such as HER 1/HER3 heterodimer receptors. CAR T-cells comprising these constructs can be used to safely and efficiently target cancer cells expressing specific protein complexes.

18 Claims, 8 Drawing Sheets

Specification includes a Sequence Listing.

(56) References Cited

OTHER PUBLICATIONS

Jena et al., Driving CAR-Based T-cell therapy to success. Curr. Hematol. Malig. Rep., 9:50-56, 2014.

Jena et al., Redirecting T-cell specificity by introducing a tumor-specific chimeric antigen receptor. Blood, 116:1035-1044, 2010.

Jiang et al., "Combination of Anti-HER3 Antibody MM-121/SAR256212 and Cetuximab Inhibits Tumor Growth in Preclinical Models of Head and Neck Squamous Cell Carcinoma (HNSCC)", *Mol Cancer Ther*, 13(7):1826-1836, 2014.

Kalos et al., T cells with chimeric antigen receptors have potent antitumor effects and can establish memory in patients with advanced leukemia. Sci. Transl. Med., 3:95ra73, 2011.

Kochenderfer et al., B-cell depletion and remissions of malignancy along with cytokine-associated toxicity in a clinical trial of anti-CD19 chimeric-antigen-receptor-transduced T cells. Blood, 119:2709-2720, 2012.

Kochenderfer et al., Eradication of B-lineage cells and regression of lymphoma in a patient treated with autologous T cells genetically engineered to recognize CD19. Blood, 116:4099-4102, 2010.

Maude et al., "Chimeric antigen receptor T cells for sustained remissions in leukemia.", *N. Engl. J. Med.*, 371:1507-1517, 2014.

Porter et al., Chimeric antigen receptor-modified T cells in chronic lymphoid leukemia. N. Engl. J. Med., 365:725-733, 2011.

Rushworth et al., "Universal Artificial antigen presenting cells to selectively propagate T cells expressing chimeric antigen receptor independent of specificity." *J. of Immunotherapy*. 37:204-213, 2014.

Sadelain et al., "The Basic Principles of Chimeric Antigen Receptor Design", *Cancer Discovery*, 3(4): 388-398, 2013.

Schaefer el al., "A Two-in-One Antibody against HER3 and EGFR Has Superior Inhibitory Activty Compared with Monospecific Antibodies." *Cancer Cell*, 20(4): 472-486, 2011.

Till et al., Adoptive immunotherapy for indolent non-Hodgkin lymphoma and mantle cell lymphoma using genetically modified autologous CD20-specific T cells. Blood, 112:2261-2271, 2008.

\* cited by examiner

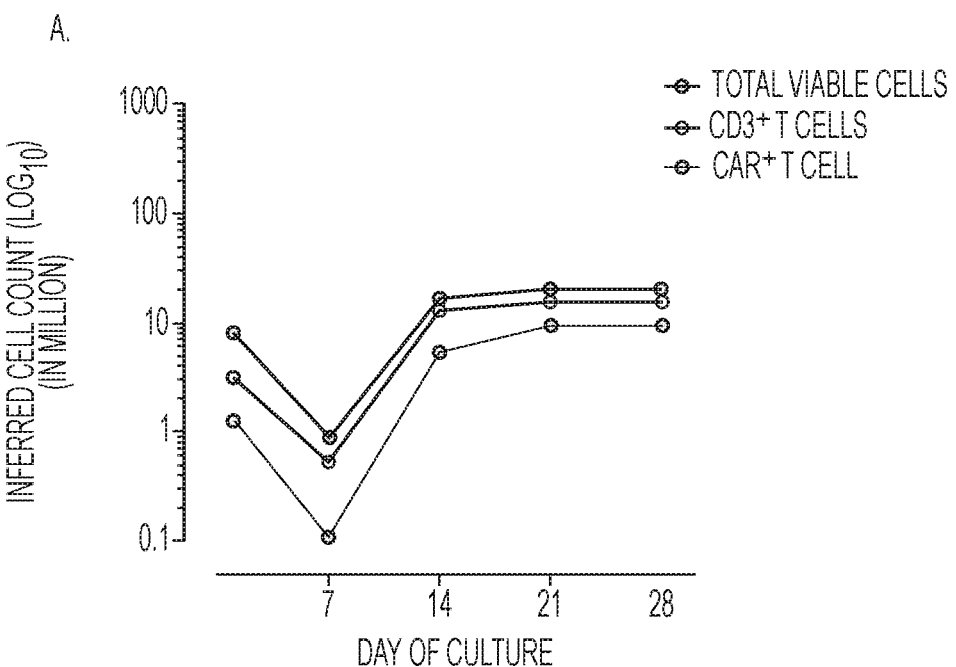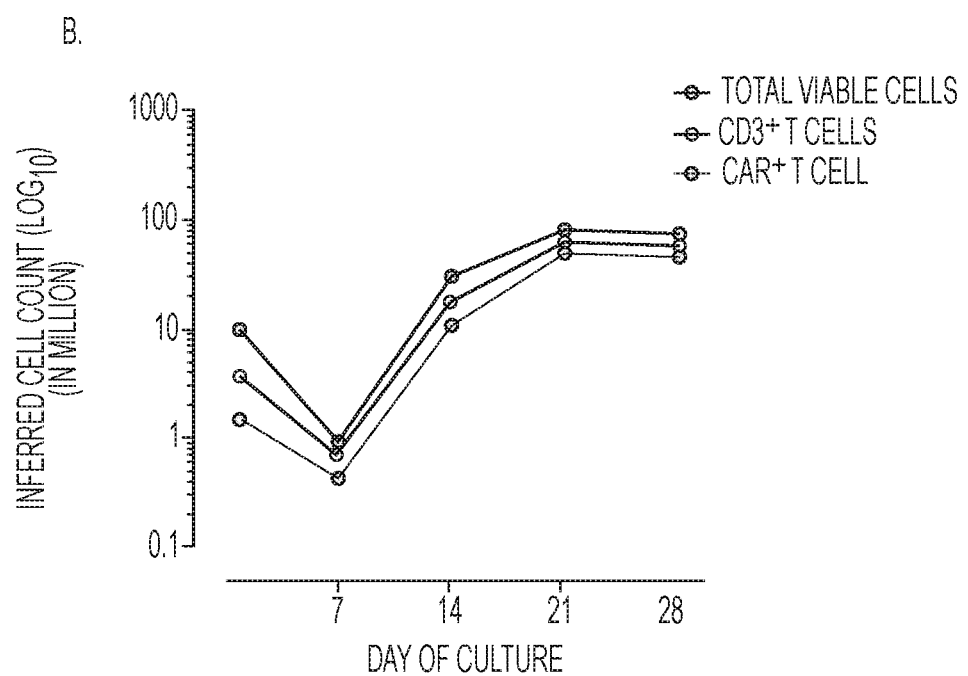
FIGS. 2A-B

MDA-MB-231
(DuoLink)
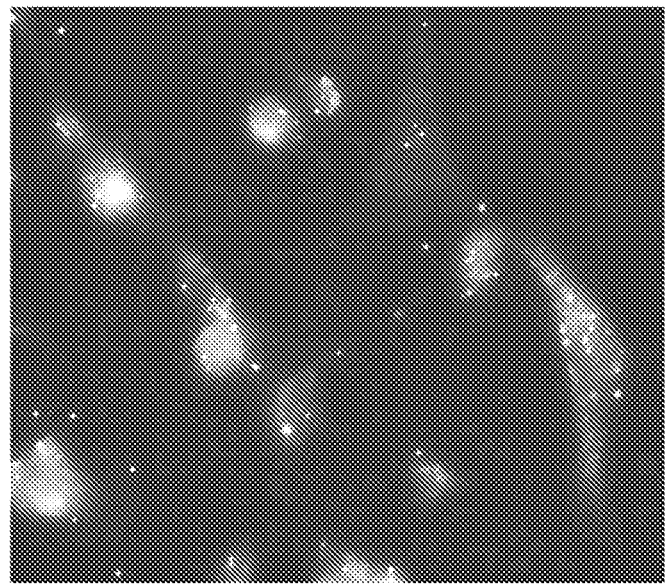
MDA-MB-231
(ANTIBODY CONTROL)
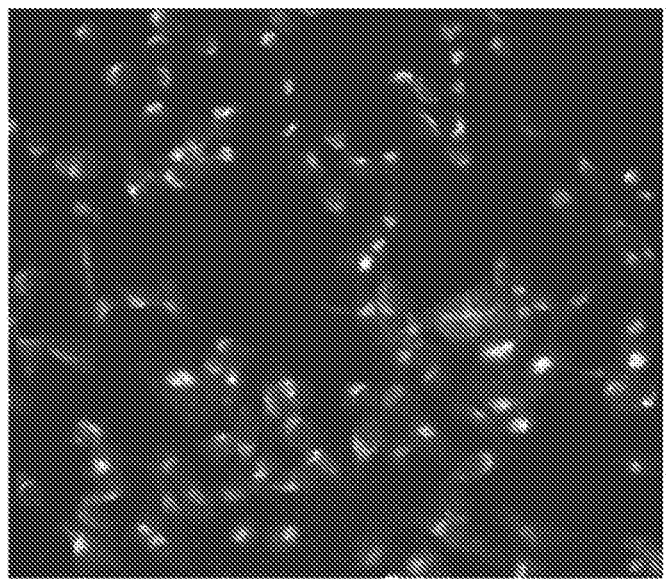
FIG. 3B

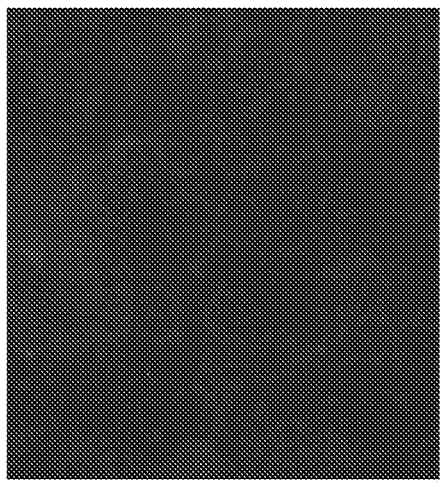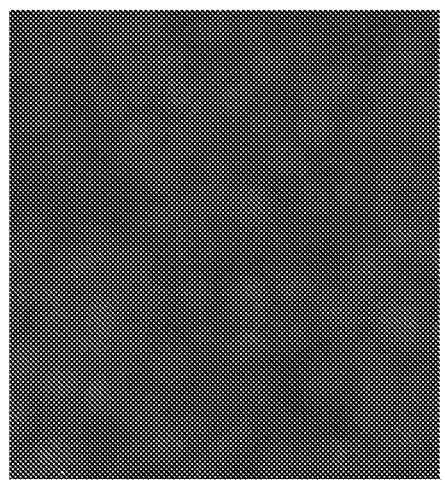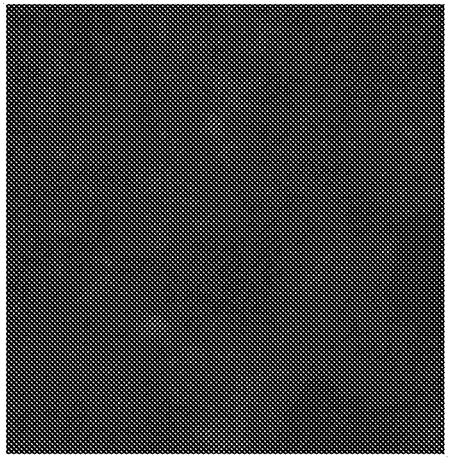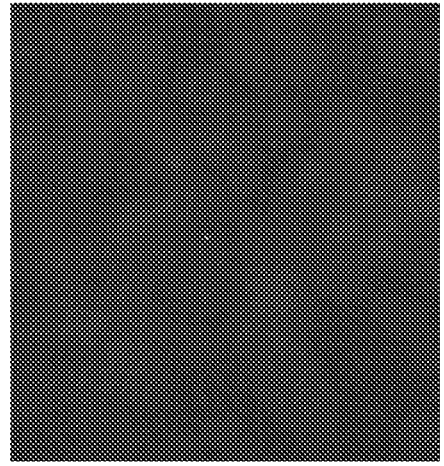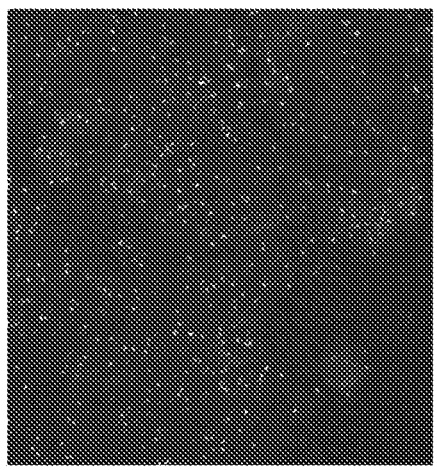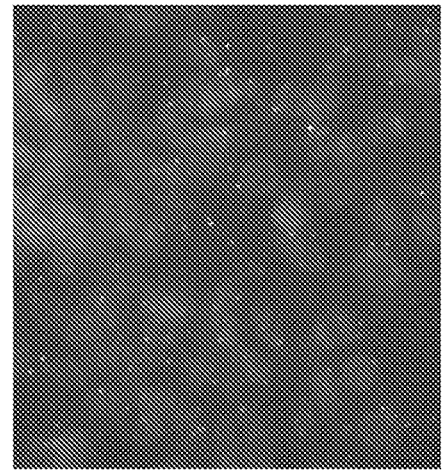
FIG. 3C

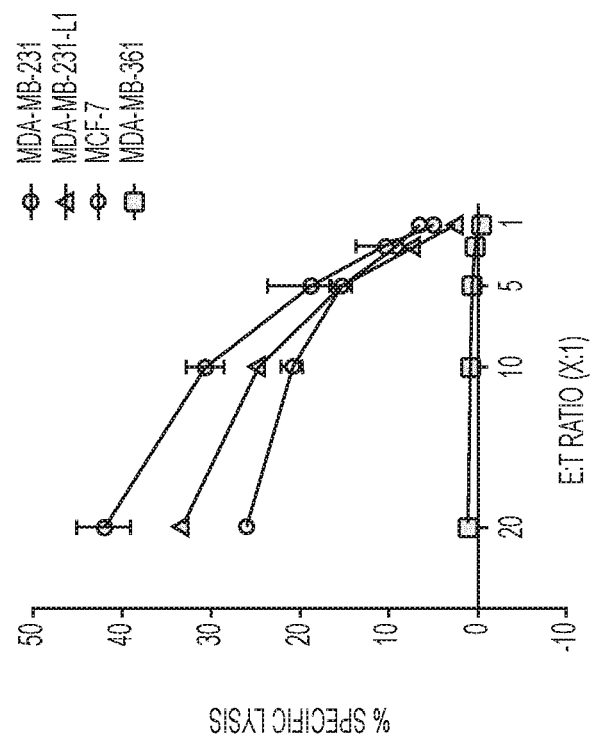
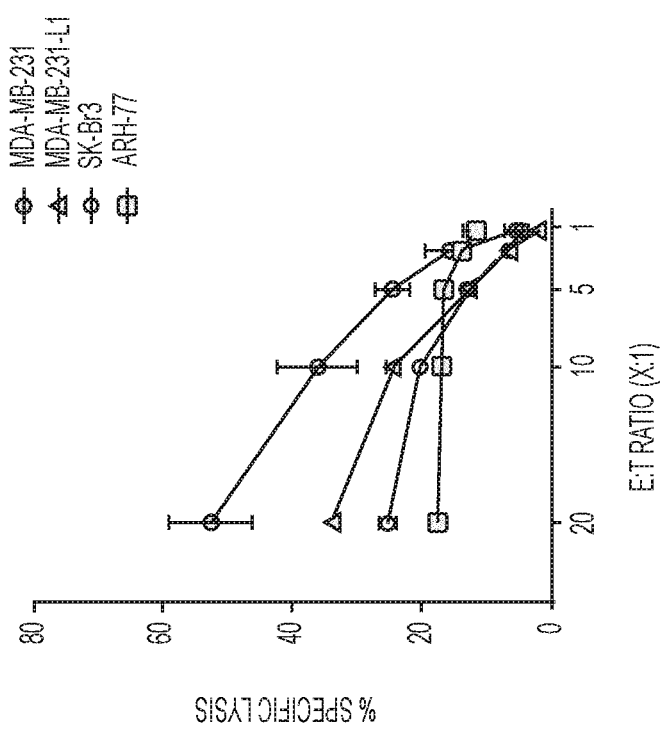
FIG. 5 ized in Microsoft Windows®) and was created on Oct. 27, 2015, is filed herewith by electronic submission and is incorporated by reference herein.

CHIMERIC ANTIGEN RECEPTORS (CAR) TO SELECTIVELY TARGET PROTEIN COMPLEXES

This application is a national phase application under 35 U.S.C. § 371 of International Application No. PCT/US2015/059072, filed Nov. 4, 2015, which claims the benefit of U.S. Provisional Patent Application No. 62/075,627, filed on Nov. 5, 2014, the entirety of which is incorporated herein by reference.

INCORPORATION OF SEQUENCE LISTING

The sequence listing that is contained in the file named "UTFCP1250WO_ST25.txt", which is 20 KB (as measured in Microsoft Windows®) and was created on Oct. 27, 2015, is filed herewith by electronic submission and is incorporated by reference herein.

BACKGROUND OF THE INVENTION

1. Field of the Invention

Described herein are chimeric antigen receptors (CAR), CAR T cells and methods of making and using CARs and CAR T cells.

2. Description of Related Art

The potency of clinical-grade T cells can be improved by combining gene therapy with immunotherapy to engineer a biologic product with the potential for superior (i) recognition of tumor-associated antigens (TAAs), (ii) persistence after infusion. (iii) potential for migration to tumor sites, and (iv) ability to recycle effector functions within the tumor microenvironment. Such genetic engineering of T cells can be used to redirect the specificity of the cells and to provide therapeutic compositions having antigen-targeted cytotoxic activity. These engineered T-cell composition have been shown to be highly effective for therapeutic intervention in, for example, cancer patients (Jena et al., 2010; Till et al., 2008; Porter et al., 2011; Brentjens et al., 2011; Cooper and Bollard, 2012; Kalos et al., 2011; Kochenderfer et al., 2010; Kochenderfer et al., 2012; Brentjens et al., 2013). There remains a need for CAR polypeptides and CAR-expressing T-cells that are highly specific to antigens, such as protein complexes, that are associated with particular diseased cells, such as cancers and its sub-types.

SUMMARY OF THE INVENTION

In a first embodiment, a chimeric antigen receptor (CAR) polypeptide is provided comprising an antigen binding domain; a hinge domain; a transmembrane domain and one or more intracellular cell signaling domain(s), wherein the antigen binding domain selectively binds to a conformational epitope of an antigen. For example, in some aspects, the antigen binding domain selectively binds to a protein complex as compared to a constituent protein of the protein complex. Examples of protein complexes include, without limitation, receptor protein complexes, protein-ligand complexes, protein-carbohydrate complex, protein-lipid complexes and protein-protein complexes. Thus, in some aspects, the protein complex is a homo or hetero dimer, trimer or tetramer protein complex. Examples of protein complexes that can be selectively bound by a CAR of the embodiments include, without limitation, CD19/CD10, CD19/CD22, CD19/ROR1, EGFR/cMET, EGFR/ROR1, GD2/ROR1 and HER1/HER3 complexes.

In various aspects, the antigen binding domain of a CAR of the embodiments may comprise a heavy chain variable domain (VH) and a light chain variable domain (VL) of a scFv or an antibody. In some aspects, the VL domain may be positioned N-terminal relative to the VH domain. In certain aspects, the VH domain may be positioned N-terminal relative to the VL domain. In certain aspects, the CAR polypeptide may further comprise a linker sequence between the VL domain and VH domain. In some aspects, the linker sequence may be a Whitlow linker.

In some embodiments, CAR polypeptides and CAR T-cells provided herein allow for the highly specific targeting of cells that express HER1/HER3 receptors. Thus, in a first embodiment, there is provided a chimeric antigen receptor (CAR) polypeptide comprising (from N- to C-terminus) an antigen binding domain, a hinge domain, a transmembrane domain and an intracellular cell signaling domain, wherein the CAR binds to HER1 and HER3 (when they form a heterodimer). In some aspects, the antigen binding domain comprises an immunoglobulin light chain variable domain and heavy chain variable domain of an antibody that binds to HER1/HER3 heterodimer. In further aspects, the scFv described herein as well as the derivative CAR binding to HER1-HER3 heterodimer occurs via specific recognition of residues placed along the HER1-3 heterodimer. In some further aspects, the CAR comprises a linker sequence (e.g., a Whitlow linker) between the light chain variable domain and heavy chain variable domain and/or the first and the second scFv domains.

In some aspects to the embodiments a hinge domain of a CAR comprises the hinge, CH2 and CH3 domains of human IgG$_4$. In further aspects, the intracellular cell signaling domain comprises a domain from CD3ζ. In further aspects, the intracellular cell signaling domain also comprises an intracellular domain from a T-cell co-stimulatory molecule, such as CD28 or CD137. In still further aspects, the transmembrane domain of a CAR may be a transmembrane domain of CD28 or CD137.

Thus, in some aspects, an antigen binding domain of a CAR comprises the immunoglobulin light chain variable domain which include CDR sequences: CDR1 (NIATDV, SEQ ID NO: 1); CDR2 (SASF, SEQ ID NO: 2); and CDR3 (SEPEPY, SEQ ID NO: 3). In some aspects, the immunoglobulin light chain variable domain is at least: 90%, 91%, 92%, 93%, 94%, 95%, 96%, 97%, 98% or 99% identical to SEQ ID NO: 4. In further aspects, the immunoglobulin light chain variable domain is identical to SEQ ID NO: 4.

In further aspects, an antigen binding domain of a CAR comprises immunoglobulin heavy chain variable domain may comprise the CDR sequences: CDR1 (LSGDW, SEQ ID NO: 5); CDR2 (EISAAGGYTD, SEQ ID NO: 6); and CDR3 (ESRVSFEAAMDY, SEQ ID NO: 7). In some aspects, the immunoglobulin heavy chain variable domain is at least: 90%, 91%, 92%, 93%, 94%, 95%, 96%, 97%, 98% or 99% identical to SEQ ID NO: 8. In further aspects, the immunoglobulin heavy chain variable domain is identical to SEQ ID NO: 8.

In still further aspects, the immunoglobulin light chain variable domain is positioned N-terminal relative to the heavy chain variable domain. Thus, a CAR of the embodiments may comprise the following domains (from N- to C-terminus) HER1/HER3-binding scFv-IgG$_4$-CH$_3$—CD137-CD3ζ. In some cases, the CAR comprises an amino acid sequence at least 90%, 91%, 92%, 93%, 94%, 95%, 96%, 97%, 98% or 99% identical to SEQ ID NO: 9. In further cases, the CAR comprises an amino acid sequence identical to SEQ ID NO: 9. Alternatively, the CAR may comprise the following domains (from N—to C-terminus) HER1/HER3-binding scFv-IgG$_4$-CH$_2$—CH$_3$—CD28-CD3ζ. In certain aspects, the CAR may only contain IgG4-Hinge-CH$_3$ only, thus devoid of CH2 domain. In some of these cases, the CAR comprises an amino acid sequence at least: 90%, 91%, 92%, 93%, 94%, 95%, 96%, 97%, 98% or 99% identical to SEQ ID NO: 10. In some cases, the CAR comprises an amino acid sequence identical to SEQ ID NO: 10.

In a further embodiment there are provided nucleic acid molecules encoding a CAR polypeptide in accordance with the first embodiment above. In some aspects, the sequence encoding the CAR is flanked by transposon repeats (IR/DR).

In yet a further embodiment there is provided an isolated immune effector cell comprising a CAR polypeptide or nucleic acid in accordance with the embodiments herein. In some aspects the cell is a T-cell, a NK cell, a NK T cell or a progenitor of one of these cell types. In further aspects, the cell is a human cell. A further embodiment provides a pharmaceutical composition comprising a population of cells in accordance with the embodiments in a pharmaceutically acceptable carrier.

In still a further embodiment, there is provided a method of treating a subject (e.g., a subject having a cancer) comprising administering an anti-tumor effective amount of CAR T-cells that expresses a CAR polypeptide in accordance with the embodiments herein. Thus, in some aspects, a subject for treatment has diseased cells that comprise protein complexes that are selectively bound by a CAR of the embodiments. For example, in some aspects, a subject may have diseased cells comprising CD19/CD10, CD19/CD22, CD19/ROR1, EGFR/cMET, EGFR/ROR1, GD2/ROR1 or HER1/HER3 complexes. In some aspects, the subject has a cancer, such as a breast cancer, ovarian cancer, melanoma, non-small cell lung cancer, gastric cancer, colorectal cancer or pancreatic cancer. In still further aspects, the subject has been identified as having a cancer that expresses HER1-HER3 protein heterodimers. In certain aspects, the cancer is resistant to at least a first therapeutic agent. For example, the cancer can be resistant to trastuzumab or a tyrosine kinase inhibitor therapy. In still further aspects, the T-cells were previously isolated from the subject.

In yet a further embodiment, there is provided a method comprising obtaining a sample of cells comprising T-cells or T-cell progenitors or other immune effector cells such as NK or NKT cells, transfecting the cells with a DNA encoding a CAR polypeptide in accordance with the embodiments, to provide a population of transgenic CAR-expressing T-cells, and culturing the population of transgenic CAR cells ex vivo in a medium that selectively enhances proliferation of CAR-expressing T-cells (e.g., co-culture with an irradiated feeder cell based system). In certain aspects, the method further comprises transfecting the cells with a transposon-flanked CAR and a transposase effective to integrate the DNA encoding the CAR into the genome of the cells. In further aspects, a method comprises purifying or enriching immune effector cells (e.g., T-cells) in the sample prior to transfection. In certain cases the immune effector cells, such as T-cells or T-cell progenitors, are derived from induced pluripotent stem cells or embryonic stem cells. In further aspects, enriching T-cells in the sample comprises collecting a mononuclear cell fraction. The sample of cells may be from umbilical cord blood, a lymphoid organ or a peripheral blood sample from the subject in some cases. The sample of cells may be obtained by apheresis or venipuncture in some cases. In still further aspects, the sample of cells is a subpopulation of T-cells. The transgenic CAR cells are inactivated for expression of an endogenous T-cell receptor and/or endogenous HLA in some aspects. Obtaining the sample of cells comprises obtaining the cells from a 3rd party in some further aspects.

In some aspects, the transfection comprises electroporating DNA encoding a CAR transgene into the T cell. The transfection may not involve infecting or transducing the cells with virus in some aspects. In still further aspects, the cells are additionally transfected with a nucleic acid encoding a membrane-bound Cγ cytokine. The membrane-bound Cγ cytokine may be a membrane bound IL-7, IL-15 or IL-21 in some instances. In a specific aspect, the membrane-bound Cγ cytokine is IL-15-IL-15Rα fusion protein.

In still further aspects, the DNA encoding the CAR is a plasmid. The transposase may be provided as a DNA expression vector, an mRNA, a polypeptide, or an expressible RNA in some aspects. In a specific aspect, the transposase is salmonid-type Tc1-like transposase (SB). In a further specific aspect, the transposase is the SB11 or SB100x transposase.

In yet a further aspect of the embodiment, culturing the transgenic CAR cells in accordance with the method of the embodiments comprises culturing the transgenic CAR cells in the presence of dendritic cells or artificial antigen presenting cells (aAPCs) or similar feeder cells that stimulate expansion of the CAR-expressing T-cells. In certain aspects, the aAPCs are transgenic K562 cells. In further aspects, the aAPCs may comprise (i) HER1, HER3, or HER1 and HER3 obligate heterodimers; (ii) CD64; (ii) CD86; (iii) CD137L; and/or (v) membrane-bound IL-15, expressed on the surface of the aAPCs. In still further aspects, the aAPCs comprise a CAR-binding antibody or fragment thereof expressed on the surface of the aAPCs. The aAPCs may comprise additional molecules that activate or co-stimulate T-cells in some cases. The additional molecules may comprise membrane-bound Cγ cytokines in some further cases. In yet still further aspects, the aAPCs are inactivated or irradiated, or have been tested for and confirmed to be free of infectious material. In still further aspects, culturing the transgenic CAR cells in the presence of aAPCs comprises culturing the transgenic CAR cells in a medium comprising IL-21 and/or IL-2. The cells may be cultured at a ratio of about 10:1 to about 1:10 (CAR cells to aAPCs) in certain cases.

In still a further aspect, culturing the population of transgenic CAR cells is for no more than 7, 14, 21, 28, 35 or 42 days. In some instances, the transgenic cells are not cultured ex vivo in the presence of aAPCs. In some specific instances, the method of the embodiment further comprises enriching the cell population for CAR-expressing T-cells after the transfection or culturing step. The enriching may comprise fluorescence-activated cell sorting (FACS) and sorting for CAR-expressing cells. In a further aspect, the sorting for CAR-expressing cells comprises use of a CAR-binding antibody. The enriching may also comprise depletion of CD56+ cells. In yet still a further aspect of the embodiment, the method further comprises cryopreserving a sample of the population of transgenic CAR cells.

In a further embodiment, there is provided a CAR T-cell population made by a method of any one of the embodiments detailed herein.

Other objects, features and advantages of the embodiments will become apparent from the following detailed description. It should be understood, however, that the detailed description and the specific examples, are given by way of illustration only, since various changes and modifi-

BRIEF DESCRIPTION OF THE DRAWINGS

FIGS. 2A-B—Ex vivo expansion of HER1-3-CD28z CAR (A) and HER1-3-CD137z CAR (B) CAR-T cells on K562$^{Cneg}$ uAPC (universal APC) bearing a CAR ligand. CAR$^+$ T cells get activation signal via stalk of the CAR only but without any T-cell co-stimulation. The proliferation of CAR$^+$ T cells is sub-optimal in absence of antigen and with minimal stimulation from APC (A). HER1-3 CD137z CAR$^+$ T cells showed better proliferation and survival on universal APC as compared to CAR-T cells containing CD28 signaling domain (B).

FIGS. 3A-C—(A) Detection of HER1-HER3 heterodimers in a representative well characterized breast cancer tumor cell line, MDA-MB-231 (fixed cells), by in situ proximity ligation assay (Duolink®). To detect HER1 and HER3 heterodimer, two separate primary antibodies (raised in different species) against HER1 and HER3 (Biolegend were used along with custom PLA probes and reagents for running circle amplification (Sigma). HER1-3 heterodimer signals are marked as precise dots on cell surface. Antibodies were titrated previously to reduce background noise. For control purposes, cells were treated with either single antibody or PLA probes only (anti-rabbit Plus and anti-mouse Minus). Detection was based on signal amplification captured digitally via fluorescence microscope (Leica DMI 6000). Images were analyzed using a Metamorph™ imaging system. An enlarged view is shown in (B). (C) HER1-HER3 heterodimers was shown in additional breast cancer cells SK-Br3 and MCF7 by in situ proximity ligation assay (Duolink®).

FIG. 5—Specific cytolytic activity of HER1-3 CAR T cells against breast tumor cells was shown after a 4-hour chromium release assay (CRA) in vitro. CAR$^+$ T cells were incubated with tumor targets labeled with chromium ($^{51}$Cr) as per standard protocol. Target cells were selected based on EGFR and HER3 expression level, presence of heterodimers as confirmed by Duolink® based proximity ligation assay. Specificity of HER1-3 CAR was ascertained through lysis of multiple BC cell lines with evidence of presence or lack of HER1-HER3 heterodimer. Specific lysis was calculated at different effector to target ratio (E:T). Data plots showed HER1-3 CAR-T cells mediated killing of breast tumor cells. Level of HER1-3 expression correlates positively with cytotoxicity. Data plots showed different level of killing based on their HER1-3 expression. HER1-3-specific CAR-T cells exhibited specific cytolytic activity against HER1-3 positive breast cancer cells.

DETAILED DESCRIPTION

Figure 1A:
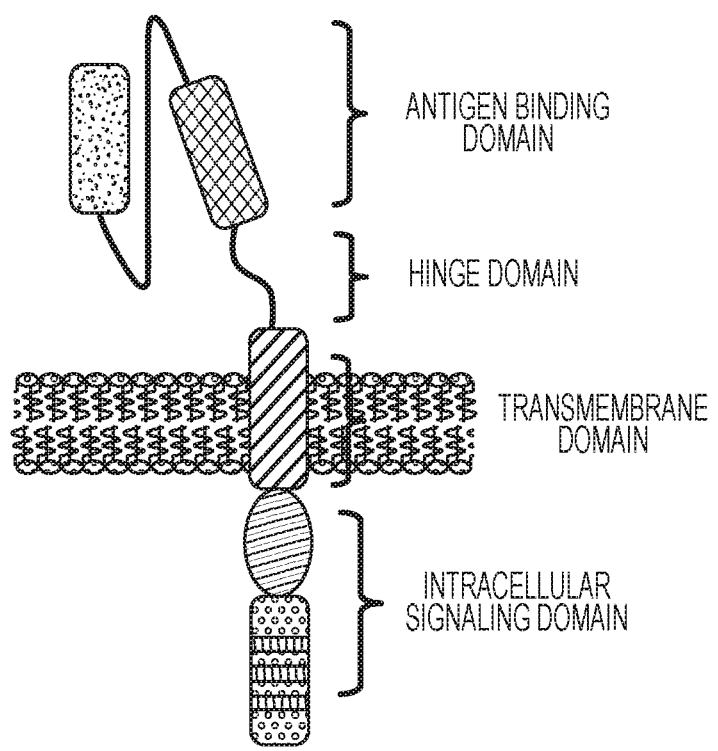
FIG. 1A-B—(A) Shows a schematic of an exemplary chimeric antigen receptor (CAR) polypeptide. The example polypeptide includes an antigen binding domain, a hinge domain, a transmembrane domain and an intracellular signaling domain. (B) Flow cytometry analysis to show expression of HER1-3 CAR on surface of genetically modified T cells. Flow plot shows emergence of CAR$^+$ T cells at Day 14 of co-culture with irradiated K562 HLA$^{Cnull}$ expressing a CAR-activating ligand. PBMCs were electroporated with DNA encoding for HER1-HER3 CAR (containing either CD28 or CD137 signaling) and propagated on irradiated AaPc (K562$^{Cneg}$ uAPC) at 1:2 ratio of CAR T cells and uAPC.

Clinical trials have demonstrated anti-tumor effects in certain patients who have received T-cells genetically modified to have desired specificity. For example, CAR-T cell therapy has been shown to deliver meaningful remission in human patients afflicted with advanced B-cell malignancies (Maude et al., 2014). This classic situation of serial killing (one T-cell killing multiple tumor cells without undergoing anergy) has been shown recently in several patients treated under various Phase I trials (Corrigan-Curay et al., 2014). However, to improve efficacy and to reduce off-target on-tissue toxicity caused by the action of CAR-T cells, there remains a need to redesign CARs that are able to target particular tumor-specific antigens, such as protein complexes, which can only be found on resistant or malignant tumors.

Studies herein demonstrate that CAR polypeptides can be selectively targeted to protein complexes that are specific to tumor cells (e.g., HER1/HER3 complexes on breast tumor). Such selectively targeted CARs enable the specific targeting of cells having specific surface receptor complexes, which may reduce the potential off-target effects of therapy. Such cells may be particularly useful in treating cancers with altered cell signaling (e.g., via receptor-activation, or through receptor cross-talk) leading to formation of cancer cells that expresses protein heterodimers such as HER1-HER3. This signaling alteration enables certain tumors to develop resistance against an otherwise effective therapy such as monoclonal antibody therapy (trastuzumab in breast cancer, for example) or against small molecule inhibitors such as tyrosine kinase inhibitors. However, the immune effector cells of the embodiments could be used to specifically target such altered cancer cells.

In some exemplary aspects, it has been shown that antibody sequences that bind to HER1/HER3 receptors (prominent on certain cancers) can be successfully adapted to a CAR to provide HER1/HER3 targeted CAR T-cells. Thus, these new CAR polypeptides and T-cells expressing the CARs can be used for specific targeting of cancer cells having elevated heterodimeric HER1 and HER3 expression.

I. Definitions

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

As used herein, the term "antigen" is a molecule capable of being bound by an antibody or T-cell receptor. An antigen is additionally capable of inducing a humoral immune response and/or cellular immune response leading to the production of B and/or T lymphocytes.

As used herein the term "anti-tumor effective amount" refers to an effective amount of CAR-expressing immune effector cells to reduce cancer cell or tumor growth or to decrease tumor volume or number of tumor cells in a subject. "An anti-tumor effective amount" can also refer to an effective amount of CAR-expressing immune effector cells to increase life expectancy or to alleviate physiological effects associated with the tumor or cancer.

II. Chimeric Antigen Receptors and Components

Chimeric antigen receptor molecules are recombinant fusion protein and are distinguished by their ability to both bind antigen (e.g., HER1/HER3) and transduce activation signals via immunoreceptor activation motifs (ITAM's) present in their cytoplasmic tails. Receptor constructs utilizing an antigen-binding moiety (for example, generated from single chain antibodies (scFv) afford the additional advantage of being "universal" in that they bind native antigen on the target cell surface in an HLA-independent fashion. An exemplary CAR polypeptide is depicted in the schematic provided at FIG. 1A.

A chimeric antigen receptor according to the embodiments can be produced by any means known in the art, though preferably it is produced using recombinant DNA techniques. A nucleic acid sequence encoding the several regions of the chimeric antigen receptor can be prepared and assembled into a complete coding sequence by standard techniques of molecular cloning (genomic library screening, PCR, primer-assisted ligation, scFv libraries from yeast and bacteria, site-directed mutagenesis, etc.). The resulting coding region can be inserted into an expression vector and used to transform a suitable expression host allogeneic or autologous immune effector cells.

Embodiments of the CARs described herein include nucleic acids encoding an antigen-specific chimeric antigen receptor (CAR) polypeptide. In some aspects, a CAR polypeptide of the embodiments comprises an antigen binding domain, such as a scFv, an intracellular signaling domain, a transmembrane domain, and an extracellular domain comprising one or more signaling motifs. In certain embodiments, the CAR may recognize an epitope comprised of the shared space between one or more antigens (e.g., a CAR may bind to heterodimer complex, but have reduced affinity for the individual components of the complex). In some embodiments, the chimeric antigen receptor comprises: a) an intracellular signaling domain, b) a transmembrane domain, and c) an extracellular domain comprising an antigen binding domain. In some embodiments, a CAR can further comprise a hinge domain positioned between the transmembrane domain and the antigen binding domain. In certain aspects, a CAR of the embodiments further comprises a signal peptide that directs expression of the CAR to the cell surface. For example, a CAR can comprise a signal peptide from GM-CSF (see, e.g., SEQ ID NO: 21).

In certain embodiments, the CAR can also be co-expressed with a membrane-bound cytokine to improve persistence when there is a low amount of tumor-associated antigen. For example, CAR can be co-expressed with membrane-bound IL-15.

A. Antigen Binding Domain

In certain embodiments, an antigen binding region can comprise complementary determining regions of a monoclonal antibody, variable regions of a monoclonal antibody, and/or antigen binding fragments thereof. In another embodiment, that specificity is derived from a peptide (e.g., cytokine) that binds to a receptor. A complementarity determining region (CDR) is a short amino acid sequence found in the variable domains of antigen receptor (e.g., immunoglobulin and T-cell receptor) proteins that complements an antigen and therefore provides the receptor with its specificity for that particular antigen. Each polypeptide chain of an antigen receptor contains three CDRs (CDR1, CDR2, and CDR3). Since the antigen receptors are typically composed of two polypeptide chains, there are six CDRs for each antigen receptor that can come into contact with the antigen—each heavy and light chain contains three CDRs. Because most sequence variation associated with immunoglobulins and T-cell receptors are found in the CDRs, these regions are sometimes referred to as hypervariable domains. Among these, CDR3 shows the greatest variability as it is encoded by a recombination of the VJ (VDJ in the case of heavy chain and TCR $\alpha\beta$ chain) regions.

It is contemplated that the CAR nucleic acids, in particular the scFv sequences, are human genes to enhance cellular immunotherapy for human patients. In a specific embodiment, there is provided a full length CAR cDNA or coding region. The antigen binding regions or domains can comprise a fragment of the VH and VL chains of a single-chain variable fragment (scFv) derived from a particular mouse, human or humanized monoclonal antibody. The fragment can also be any number of different antigen binding domains of an antigen-specific antibody. In a more specific embodiment, the fragment is an antigen-specific scFv encoded by a sequence that is optimized for human codon usage for expression in human cells. In certain aspects, VH and VL domains of a CAR are separated by a linker sequence, such as a Whitlow linker (see, e.g., SEQ ID NO: 20).

In some specific examples the antigen binding domain of a CAR is specific for binding to a heterodimeric complex. Examples of heterodimeric complexes include but are not limited to CD19/CD10, CD19/CD22, CD19/ROR1, EGFR/cMET, EGFR/ROR1, GD2/ROR1 or HER1/HER3 heterodimeric complexes. In some aspects, a subject may have diseased cells comprising CD19/CD10, CD19/CD22, CD19/ROR1, EGFR/cMET, EGFR/ROR1, GD2/ROR1 or HER1/HER3 heterodimeric complexes.

In certain embodiments of the chimeric antigen receptor, the antigen-specific portion of the receptor (which may be referred to as an extracellular domain comprising an antigen binding region) comprises a HER1/HER3 binding domain as detailed herein above. In some aspects, for example, the HER1/HER3 binding domain comprises one of the sequences provided in U.S. Patent Publication No. 2012/0121596, incorporated herein by reference.

B. Hinge Domain

In certain aspects, stalk of a CAR polypeptide of the embodiments can include a hinge domain positioned between the antigen binding domain and the transmembrane domain. In some cases, a hinge domain may be included in CAR polypeptides to provide adequate distance between the antigen binding domain and the cell surface or to alleviate possible steric hindrance that could adversely affect antigen binding or effector function of CAR-gene modified T cells.

In some cases the CAR hinge domain can be derived from human immunoglobulin (Ig) constant region or a portion thereof including the Ig hinge, or from human CD8 $\alpha$ transmembrane domain and CD8$\alpha$-hinge region. In one aspect, the CAR hinge domain can comprise a hinge-$CH_2$—$CH_3$ region of antibody isotype $IgG_4$. In some aspects, point mutations can be introduced in antibody heavy chain $CH_2$ domain to reduce glycosylation and non-specific Fc gamma receptor binding of CAR-T cells or any other CAR-modified cells.

In certain specific aspects, the hinge domain comprises a sequence 85%, 90%, 91%, 92%, 93%, 94%, 95%, 96%, 97%, 98%, 99% or 100% identical to an IgG4-Fe domain of SEQ ID NO: 16 or SEQ ID NO: 17, a CD8α extracellular domain of SEQ ID NO: 18 or a synthetic hinge sequence of SEQ ID NO: 19.

C. Transmembrane Domain

The antigen-specific extracellular domain and the intracellular signaling-domain may be linked by a transmembrane domain. Polypeptide sequences that can be used as part of transmembrane domain include, without limitation, the human CD4 transmembrane domain, the human CD28 transmembrane domain, the transmembrane human CD3ζ domain, or a cysteine mutated human CD3ζ domain, or other transmembrane domains from other human transmembrane signaling proteins, such as CD16 and CD8 and erythropoietin receptor. In some aspects, for example, the transmembrane domain comprises one of the sequences provided in U.S. Patent Publication No. 2014/0274909 or U.S. Pat. No. 8,906,682, both incorporated herein by reference. In certain specific aspects, the transmembrane domain can be 85%, 90%, 91%, 92%, 93%, 94%, 95%, 96%, 97%, 98%, 99% or 100% identical to a CD8α transmembrane domain of SEQ ID NO: 11 or a CD28 transmembrane domain of SEQ ID NO: 12.

D. Intracellular Signaling Domain

The intracellular signaling domain of the chimeric antigen receptor of the embodiments is responsible for activation of at least one of the normal effector functions of the immune cell engineered to express a chimeric antigen receptor. The term "effector function" refers to a specialized function of a differentiated cell. Effector function of a T cell, for example, may be cytolytic activity or helper activity including the secretion of cytokines. Effector function in a naive, memory, or memory-type T cell includes antigen-dependent proliferation. Thus the term "intracellular signaling domain" refers to the portion of a protein that transduces the effector function signal and directs the cell to perform a specialized function. In some aspects, the intracellular signaling domain is derived from the intracellular signaling domain of a native receptor. Examples of such native receptors include the zeta chain of the T-cell receptor or any of its homologs (e.g., eta, delta, gamma, or epsilon), MB1 chain, B29, Fc RIII, Fc RI, and combinations of signaling molecules, such as CD3ζ and CD28, CD27, 4-1BB, DAP-10, OX40, and combinations thereof, as well as other similar molecules and fragments. Intracellular signaling portions of other members of the families of activating proteins can be used, such as FcγRIII and FcεRI. See Gross et al. (1992), Stancovski et al. (1993), Moritz et al. (1994), Hwu et al. (1995), Weijtens et al. (1996), and Hekele et al. (1996) for disclosures of T-cell receptors using these alternative transmembrane and intracellular domains. While usually the entire intracellular signaling domain will be employed, in many cases it will not be necessary to use the entire intracellular polypeptide. To the extent that a truncated portion of the intracellular signaling domain may find use, such truncated portion may be used in place of the intact chain as long as it still transduces the effector function signal. The term "intracellular signaling domain" is thus meant to include a truncated portion of the intracellular signaling domain sufficient to transduce the effector function signal, upon CAR binding to a target. In a preferred embodiment, the human CD3ζ intracellular domain is used as the intracellular signaling domain for a CAR of the embodiments.

In specific embodiments, intracellular receptor signaling domains in the CAR include those of the T cell antigen receptor complex, such as the ζ chain of CD3, also Fcγ RIII costimulatory signaling domains, CD28, CD27, DAP10, CD137, OX40, CD2, alone or in a series with CD3ζ, for example. In specific embodiments, the intracellular domain (which may be referred to as the cytoplasmic domain) comprises part or all of one or more of TCRζ chain, CD28, CD27, OX40/CD134, 4-1BB/CD137, FcεRIγ, ICOS/CD278, IL-2Rβ/CD122, IL-2Rα/CD132, DAP10, DAP12, and CD40. In some embodiments, one employs any part of the endogenous T cell receptor complex in the intracellular domain. One or multiple cytoplasmic domains may be employed, as so-called third generation CARs have at least two or three signaling domains fused together for additive or synergistic effect, for example.

In some embodiments, the CAR comprises additional other costimulatory domains. Other costimulatory domains can include, but are not limited to one or more of CD28, CD27, OX-40 (CD134), DAP10, and 4-1BB (CD137). In addition to a primary signal initiated by CD3ζ, an additional signal provided by a human costimulatory receptor inserted in a human CAR is important for full activation of T cells and could help improve in vivo persistence and the therapeutic success of the adoptive immunotherapy.

In certain specific aspects, the intracellular signaling domain comprises a sequence 85%, 90%, 91%, 92%, 93%, 94%, 95%, 96%, 97%, 98%, 99% or 100% identical to a CD3ζ intracellular domain of SEQ ID NO: 13, a CD28 intracellular domain of SEQ ID NO: 14 or a CD137 intracellular domain of SEQ ID NO: 15.

III. Vectors and Cell Engineering

In particular embodiments, isolated nucleic acid segments and expression cassettes incorporating DNA sequences that encode a CAR are provided. As will be appreciated by one of skill in the art that, in some instances, a few amino acids at the ends of the antigen binding domain in the CAR can be deleted without affecting either specificity or effector binding affinity of the molecule, usually not more than 10, more usually not more than 5 residues, for example. Also, it may be desirable to introduce a small number of amino acids at the borders, usually not more than 10, more usually not more than 5 residues. The deletion or insertion of amino acids may be as a result of the needs of the construction, providing for convenient restriction sites, ease of manipulation, improvement in levels of expression, or the like. In addition, the substitute of one or more amino acids with a different amino acid can occur for similar reasons, usually not substituting more than about 5 amino acids in any one domain.

The chimeric construct that encodes the chimeric antigen receptor according to the embodiments can be prepared in conventional ways. Because, for the most part, natural sequences may be employed, the natural genes may be isolated and manipulated, as appropriate, so as to allow for the proper joining of the various components. Thus, the nucleic acid sequences encoding for the N-terminal and C-terminal protein components of the chimeric antigen receptor can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired chimeric antigen receptor. The sequence can be screened by restriction analysis, sequencing, or the like.

Vectors of the embodiments designed, primarily, to deliver desired genes to immune cells, preferably T cells, under the control of regulated eukaryotic promoters, for example, MNDU3 promoter, CMV promoter, EF1α promoter, or Ubiquitin promoter. Also, the vectors may contain a selectable marker, if for no other reason, to facilitate their manipulation in vitro. In other embodiments, the CAR can be expressed from mRNA in vitro transcribed from a DNA template.

In an exemplary nucleic acid construct (polynucleotide) employed according to the embodiments, the promoter is operably linked to the nucleic acid sequence encoding a chimeric antigen receptor of the embodiments, i.e., they are positioned so as to promote transcription of the messenger RNA from the DNA encoding the chimeric antigen receptor. The promoter can be of genomic origin or synthetically generated. A variety of promoters for use in T cells are well-known in the art (e.g., the CD4 promoter disclosed by Marodon et al. (2003)). The promoter can be constitutive or inducible, where induction is associated with the specific cell type or a specific level of maturation, for example. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter. The promoters may or may not be associated with enhancers, wherein the enhancers may be naturally associated with the particular promoter or associated with a different promoter.

The sequence of the open reading frame encoding the chimeric antigen receptor can be obtained from a genomic DNA source, a cDNA source, or can be synthesized (e.g., via PCR), or combinations thereof. Depending upon the size of the genomic DNA and the number of introns, it may be desirable to use cDNA or a combination thereof as it is found that introns stabilize the mRNA or provide T cell-specific expression (Barthel and Goldfeld, 2003). Also, it may be further advantageous to use endogenous or exogenous non-coding regions to stabilize the mRNA.

For expression of a chimeric antigen receptor of the embodiments, the naturally occurring or endogenous transcriptional initiation region of the nucleic acid sequence encoding N-terminal components of e.g., a T-cell receptor can be used to generate the chimeric antigen receptor in the target host. Alternatively, an exogenous transcriptional initiation region can be used that allows for constitutive or inducible expression, wherein expression can be controlled depending upon the target host, the level of expression desired, the nature of the target host, and the like.

Likewise, a signal sequence directing the chimeric antigen receptor to the surface membrane can be the endogenous signal sequence of T-cell receptor. Optionally, in some instances, it may be desirable to exchange this sequence for a different signal sequence. However, the signal sequence selected should be compatible with the secretory pathway of T cells so that the chimeric antigen receptor is presented on the surface of the T cell.

Similarly, a termination region may be provided by the naturally occurring or endogenous transcriptional termination region for a T-cell receptor subunit. Alternatively, the termination region may be derived from a different source. For the most part, the source of the termination region is generally not considered to be critical to the expression of a recombinant protein and a wide variety of termination regions can be employed without adversely affecting expression.

It is contemplated that the CAR construct can be introduced into the subject's own cells (or into cells from a different donor subject) as naked DNA or in a suitable vector. Methods of stably transfecting T cells by electroporation using naked DNA are known in the art. See, for example, U.S. Pat. No. 6,410,319, incorporated herein by reference. Naked DNA generally refers to the DNA encoding a chimeric antigen receptor of the present embodiments contained in a plasmid expression vector in proper orientation for expression. Advantageously, the use of naked DNA can reduce the time required to produce T cells expressing the chimeric antigen receptor of the embodiments.

In further aspects, CAR constructs can be introduced into cells using a transposon-based system to mediate integration of the CAR construct into genomic DNA of the cells. Generally, such methods will involve introducing into cells (i) a first vector encoding the transposase (or a transposase polypeptide) and (ii) a second vector encoding a desired genetic element that is flanked by transposon repeats. Transposons or transposable elements include a (short) nucleic acid sequence with terminal repeat sequences upstream and downstream thereof and encode enzymes that facilitate the excision and insertion of the nucleic acid into target DNA sequences. Several transposon/transposase systems have been adapted for genetic insertions of heterologous DNA sequences, including Sleeping Beauty (SB), a Tc1/mariner-like element from fish that exhibits transpositional activity in a variety of vertebrate cultured cell lines, embryonic stem cells and in vivo (Ivics et al., 1997). Additional transposases and transposon systems are provided in U.S. Pat. Nos. 6,489,458; 7,148,203; 8,227,432; U.S. Patent Publn. No. 2011/0117072; Mates et al., 2009 and in Ivies et al., 1997, each of which are incorporated herein by reference in their entirety.

Alternatively, a viral vector (e.g., a retroviral vector, adenoviral vector, adeno-associated viral vector, or lentiviral vector) can be used to introduce the chimeric construct into T cells. Suitable vectors for use in accordance with the method of the embodiments are non-replicating in the subject's T cells. A large number of vectors are known that are based on viruses, where the copy number of the virus maintained in the cell is low enough to maintain the viability of the cell. Illustrative vectors include the pFB-neo vectors (STRATAGENE®) disclosed herein as well as vectors based on HIV, SV40, EBV, HSV, or BPV.

IV. Immune Effector Cells

In certain aspects, the embodiments described herein include methods of making and/or expanding the antigen-specific redirected immune effector cells (e.g., T-cells. NK-cell or NK T-cells) that comprises transfecting the cells with an expression vector containing a DNA (or RNA) construct encoding the CAR, then, optionally, stimulating the cells with feeder cells, recombinant antigen, or an antibody to the receptor to cause the cells to proliferate. In certain aspects, the cell (or cell population) engineered to express a CAR is a stem cell, iPS cell, immune cell or a precursor of these cells. Methods described below address the specific example of T-cells (or other immune cell) engineering for CAR expression.

Sources of immune effector cells include both allogeneic and autologous sources. In some cases immune effector cells may be differentiated from stem cells or induced pluripotent stem cells (iPSCs). Thus, the immune effector cells according to the embodiments can be isolated from umbilical cord blood, peripheral blood, human embryonic stem cells, or iPSCs. For example, allogeneic T cells can be modified to include a chimeric antigen receptor (and optionally, to lack functional TCR). In some aspects, the immune effector cells are primary human T cells, such as T cells derived from human peripheral blood mononuclear cells (PBMC), PBMC collected after stimulation with G-CSF, bone marrow, or umbilical cord blood. Following transfection or transduction (e.g., with a CAR expression construct), the cells may be immediately infused or may be stored. In certain aspects, following transfection, the cells may be propagated for days, weeks, or months ex vivo as a bulk population within about 1, 2, 3, 4, 5 days or more following gene transfer into cells. In a further aspect, following transfection, the transfectants are cloned and a clone demonstrating presence of a single integrated or episomally maintained expression cassette or plasmid, and expression of the chimeric antigen receptor is expanded ex vivo. The clone selected for expansion demonstrates the capacity to specifically recognize and lyse antigen-expressing target cells. The recombinant T cells may be expanded by stimulation with IL-2, or other cytokines that bind the common gamma-chain (e.g., IL-7, IL-12, IL-15, IL-21, and others). The recombinant T cells may be expanded by stimulation with artificial antigen presenting cells. The recombinant T cells may be expanded on artificial antigen presenting cell or with an antibody, such as OKT3, which cross links CD3 on the T cell surface. Subsets of the recombinant T cells may be deleted on artificial antigen presenting cell or with an antibody, such as Campath, which binds CD52 on the T cell surface. In a further aspect, the genetically modified cells may be cryopreserved.

V. Method for Propagating Immune Effector Cells

In some cases, immune effector cells of the embodiments (e.g., T-cells) are co-cultured with activating and propagating cells (AaPCs), to aid in cell expansion. For example, antigen presenting cells (APCs) are useful in preparing therapeutic compositions and cell therapy products of the embodiments. For general guidance regarding the preparation and use of antigen-presenting systems, see, e.g., U.S. Pat. Nos. 6,225,042, 6,355,479, 6,362,001 and 6,790,662; U.S. Patent Application Publication Nos. 2009/0017000 and 2009/0004142; and International Publication No. WO2007/103009, each of which is incorporated by reference.

In some cases, AaPCs are incubated with a peptide of an optimal length that allows for direct binding of the peptide to the MHC molecule without additional processing. Alternatively, the cells can express an antigen of interest (i.e., in the case of MHC-independent antigen recognition). Furthermore, in some cases, APCs can express an antibody that binds to either a specific CAR polypeptide or to CAR polypeptides in general (e.g., a universal activating and propagating cell (uAPC). Such methods are disclosed in International (PCT) Patent Pub. No. WO/2014/190273, which is incorporated herein by reference. In addition to peptide-MHC molecules or antigens of interest, the AaPC systems may also comprise at least one exogenous assisting molecule. Any suitable number and combination of assisting molecules may be employed. The assisting molecule may be selected from assisting molecules such as co-stimulatory molecules and adhesion molecules. Exemplary co-stimulatory molecules include CD70 and B7.1 (B7.1 was previously known as B7 and also known as CD80), which among other things, bind to CD28 and/or CTLA-4 molecules on the surface of T cells, thereby affecting, for example, T-cell expansion, Th1 differentiation, short-term T-cell survival, and cytokine secretion such as interleukin (IL)-2 (see Kim et al., 2004). Adhesion molecules may include carbohydrate-binding glycoproteins such as selectins, transmembrane binding glycoproteins such as integrins, calcium-dependent proteins such as cadherins, and single-pass transmembrane immunoglobulin (Ig) superfamily proteins, such as intercellular adhesion molecules (ICAMs), that promote, for example, cell-to-cell or cell-to-matrix contact. Exemplary adhesion molecules include LFA-3 and ICAMs, such as ICAM-1. Techniques, methods, and reagents useful for selection, cloning, preparation, and expression of exemplary assisting molecules, including co-stimulatory molecules and adhesion molecules, are exemplified in, e.g., U.S. Pat. Nos. 6,225,042, 6,355,479, and 6,362,001, incorporated herein by reference.

Cells selected to become AaPCs, preferably have deficiencies in intracellular antigen-processing, intracellular peptide trafficking, and/or intracellular MHC Class I or Class 11 molecule-peptide loading, or are poikilothermic (i.e., less sensitive to temperature challenge than mammalian cell lines), or possess both deficiencies and poikilothermic properties. Preferably, cells selected to become AaPCs also lack the ability to express at least one endogenous counterpart (e.g., endogenous MHC Class I or Class II molecule and/or endogenous assisting molecules as described above) to the exogenous MHC Class I or Class II molecule and assisting molecule components that are introduced into the cells. Furthermore, AaPCs preferably retain the deficiencies and poikilothermic properties that were possessed by the cells prior to their modification to generate the AaPCs. Exemplary AaPCs either constitute or are derived from a transporter associated with antigen processing (TAP)-deficient cell line, such as an insect cell line. An exemplary poikilothermic insect cells line is a *Drosophila* cell line, such as a Schneider 2 cell line (see, e.g., Schneider 1972 Illustrative methods for the preparation, growth, and culture of Schneider 2 cells, are provided in U.S. Pat. Nos. 6,225,042, 6,355,479, and 6,362,001.

In one embodiment, AaPCs are also subjected to a freeze-thaw cycle. In an exemplary freeze-thaw cycle, the AaPCs may be frozen by contacting a suitable receptacle containing the AaPCs with an appropriate amount of liquid nitrogen, solid carbon dioxide (i.e., dry ice), or similar low-temperature material, such that freezing occurs rapidly. The frozen APCs are then thawed, either by removal of the AaPCs from the low-temperature material and exposure to ambient room temperature conditions, or by a facilitated thawing process in which a lukewarm water bath or warm hand is employed to facilitate a shorter thawing time. Additionally, AaPCs may be frozen and stored for an extended period of time prior to thawing. Frozen AaPCs may also be thawed and then lyophilized before further use. Preferably, preservatives that might detrimentally impact the freeze-thaw procedures, such as dimethyl sulfoxide (DMSO), polyethylene glycols (PEGs), and other preservatives, are absent from media containing AaPCs that undergo the freeze-thaw cycle, or are essentially removed, such as by transfer of AaPCs to media that is essentially devoid of such preservatives.

In further embodiments, xenogenic nucleic acid and nucleic acid endogenous to the AaPCs, may be inactivated by crosslinking, so that essentially no cell growth, replication or expression of nucleic acid occurs after the inactivation. In one embodiment, AaPCs are inactivated at a point subsequent to the expression of exogenous MHC and assisting molecules, presentation of such molecules on the surface of the AaPCs, and loading of presented MHC molecules with selected peptide or peptides. Accordingly, such inactivated and selected peptide loaded AaPCs, while rendered essentially incapable of proliferating or replicating, retain selected peptide presentation function. Preferably, the crosslinking also yields AaPCs that are essentially free of contaminating microorganisms, such as bacteria and viruses, without substantially decreasing the antigen-presenting cell function of the AaPCs. Thus crosslinking maintains the important AaPC functions of while helping to alleviate concerns about safety of a cell therapy product developed using the AaPCs. For methods related to crosslinking and AaPCs, see for example, U.S. Patent Application Publication No. 20090017000, which is incorporated herein by reference.

In certain cases, CAR modified cells can be sorted based on their mitochondrial strength (or total mitochondria content of the cells) by employing a fluorescent reporter protein using FACS prior to use as a therapeutic.

VI. Therapeutic Application

In some aspects, the chimeric antigen receptor constructs of the embodiments find application in subjects having or suspected of having cancer by reducing the size of a tumor or preventing the growth or re-growth of a tumor in these subjects. Accordingly, embodiments of provided herein further relate to a method for reducing growth or preventing tumor formation in a subject by introducing a chimeric antigen receptor construct of the present embodiments into an isolated T cell of the subject and reintroducing into the subject the transformed T cell, thereby effecting anti-tumor responses to reduce or eliminate tumors in the subject. Suitable T cells that can be used include cytotoxic lymphocytes (CTL) or any cell having a T cell receptor in need of disruption. As is well-known to one of skill in the art, various methods are readily available for isolating these cells from a subject. For example, using cell surface marker expression or using commercially available kits (e.g., ISO-CELL™ from Pierce, Rockford, Ill.).

Once it is established that the transfected or transduced immune effector cell (e.g., T cell) is capable of expressing the chimeric antigen receptor as a surface membrane protein with the desired regulation and at a desired level, it can be determined whether the chimeric antigen receptor is functional in the host cell to provide for the desired signal induction. Subsequently, the transduced immune effector cells are reintroduced or administered to the subject to activate anti-tumor responses in the subject. To facilitate administration, the transduced T cells according to the embodiments can be made into a pharmaceutical composition or made into an implant appropriate for administration in vivo, with appropriate carriers or diluents, which further can be pharmaceutically acceptable. The means of making such a composition or an implant have been described in the art (see, for instance, Remington's Pharmaceutical Sciences, 16th Ed., Mack, ed. (1980)). Where appropriate, the transduced T cells can be formulated into a preparation in semisolid or liquid form, such as a capsule, solution, injection, inhalant, or aerosol, in the usual ways for their respective route of administration. Means known in the art can be utilized to prevent or minimize release and absorption of the composition until it reaches the target tissue or organ, or to ensure timed-release of the composition. Desirably, however, a pharmaceutically acceptable form is employed that does not ineffectuate the cells expressing the chimeric antigen receptor. Thus, desirably the transduced T cells can be made into a pharmaceutical composition containing a balanced salt solution, preferably Hanks' balanced salt solution, or normal saline.

In certain embodiments, CAR-expressing cells of the embodiments are delivered to an individual in need thereof, such as an individual that has cancer or an infection. The cells then enhance the individual's immune system to attack the respective cancer or pathogen-infected cells. In some cases, the individual is provided with one or more doses of the antigen-specific CAR cells. In cases where the individual is provided with two or more doses of the antigen-specific CAR cells, the duration between the administrations should be sufficient to allow time for propagation in the individual, and in specific embodiments the duration between doses is 1, 2, 3, 4, 5, 6, 7, or more days. Suitable doses for a therapeutic effect would be at least $10^5$ or between about $10^5$ and about $10^{10}$ cells per dose, for example, preferably in a series of dosing cycles. An exemplary dosing regimen consists of four one-week dosing cycles of escalating doses, starting at least at about $10^5$ cells on Day 0, for example increasing incrementally up to a target dose of about $10^{10}$ cells within several weeks of initiating an intra-patient dose escalation scheme. Suitable modes of administration include intravenous, subcutaneous, intracavitary (for example by reservoir-access device), intraperitoneal, and direct injection into a tumor mass.

A pharmaceutical composition of the embodiments (e.g., comprising CAR-expressing T-cells) can be used alone or in combination with other well-established agents useful for treating cancer. Whether delivered alone or in combination with other agents, the pharmaceutical composition of the embodiments can be delivered via various routes and to various sites in a mammalian, particularly human, body to achieve a particular effect. One skilled in the art will recognize that, although more than one route can be used for administration, a particular route can provide a more immediate and more effective reaction than another route. For example, intradermal delivery may be used for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

A composition of the embodiments can be provided in unit dosage form wherein each dosage unit, e.g., an injection, contains a predetermined amount of the composition, alone or in appropriate combination with other active agents. The term unit dosage form as used herein refers to physically discrete units suitable as unitary dosages for human and animal subjects, each unit containing a predetermined quantity of the composition of the embodiments, alone or in combination with other active agents, calculated in an amount sufficient to produce the desired effect, in association with a pharmaceutically acceptable diluent, carrier, or vehicle, where appropriate. The specifications for the novel unit dosage forms of the embodiments depend on the particular pharmacodynamics associated with the pharmaceutical composition in the particular subject.

Desirably an effective amount or sufficient number of the isolated transduced T cells is present in the composition and introduced into the subject such that long-term, specific, anti-tumor responses are established to reduce the size of a tumor or eliminate tumor growth or regrowth than would otherwise result in the absence of such treatment. Desirably, the amount of transduced T cells reintroduced into the subject causes a 10%, 20%, 30%, 40%, 50%, 60%, 70%, 80%, 90%, 95%, 98%, or 100% decrease in tumor size when compared to otherwise same conditions wherein the transduced T cells are not present. As used herein the term "anti-tumor effective amount" refers to an effective amount of CAR-expressing immune effector cells to reduce cancer cell or tumor growth in a subject.

Accordingly, the amount of transduced immune effector cells (e.g., T cells) administered should take into account the route of administration and should be such that a sufficient number of the transduced immune effector cells will be introduced so as to achieve the desired therapeutic response. Furthermore, the amounts of each active agent included in the compositions described herein (e.g., the amount per each cell to be contacted or the amount per certain body weight) can vary in different applications. In general, the concentration of transduced T cells desirably should be sufficient to provide in the subject being treated at least from about $1 \times 10^6$ to about $1 \times 10^9$ transduced T cells, even more desirably, from about $1 \times 10^7$ to about $5 \times 10^8$ transduced T cells, although any suitable amount can be utilized either above, e.g., greater than $5 \times 10^8$ cells, or below, e.g., less than $1 \times 10^7$ cells. The dosing schedule can be based on well-established cell-based therapies (see, e.g., Topalian and Rosenberg, 1987; U.S. Pat. No. 4,690,915), or an alternate continuous infusion strategy can be employed.

These values provide general guidance of the range of transduced T cells to be utilized by the practitioner upon optimizing the method of the embodiments. The recitation herein of such ranges by no means precludes the use of a higher or lower amount of a component, as might be warranted in a particular application. For example, the actual dose and schedule can vary depending on whether the compositions are administered in combination with other pharmaceutical compositions, or depending on inter-individual differences in pharmacokinetics, drug disposition, and metabolism. One skilled in the art readily can make any necessary adjustments in accordance with the exigencies of the particular situation.

VII. Kits of the Embodiments

Any of the compositions described herein may be comprised in a kit. In some embodiments, allogeneic CAR T-cells are provided in the kit, which also may include reagents suitable for expanding the cells, such as media, APCs, growth factors, antibodies (e.g., for sorting or characterizing CAR T-cells) and/or plasmids encoding CARs or transposase.

In a non-limiting example, a chimeric antigen receptor expression construct, one or more reagents to generate a chimeric antigen receptor expression construct, cells for transfection of the expression construct, and/or one or more instruments to obtain allogeneic cells for transfection of the expression construct (such an instrument may be a syringe, pipette, forceps, and/or any such medically approved apparatus).

In some embodiments, an expression construct for eliminating endogenous TCR α/β expression, one or more reagents to generate the construct, and/or CAR+ T cells are provided in the kit. In some embodiments, there includes expression constructs that encode zinc finger nuclease(s).

In some aspects, the kit comprises reagents or apparatuses for electroporation of cells.

The kits may comprise one or more suitably aliquoted compositions of the embodiments or reagents to generate compositions of the embodiments. The components of the kits may be packaged either in aqueous media or in lyophilized form. The container means of the kits may include at least one vial, test tube, flask, bottle, syringe, or other container means, into which a component may be placed, and preferably, suitably aliquoted. Where there is more than one component in the kit, the kit also will generally contain a second, third, or other additional container into which the additional components may be separately placed. However, various combinations of components may be comprised in a vial. The kits of the embodiments also will typically include a means for containing the chimeric antigen receptor construct and any other reagent containers in close confinement for commercial sale. Such containers may include injection or blow molded plastic containers into which the desired vials are retained, for example.

VIII. Examples

The embodiments of the invention are further described in detail by reference to the following examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

Example 1

Flow Cytometry Analysis

Figure 1B:
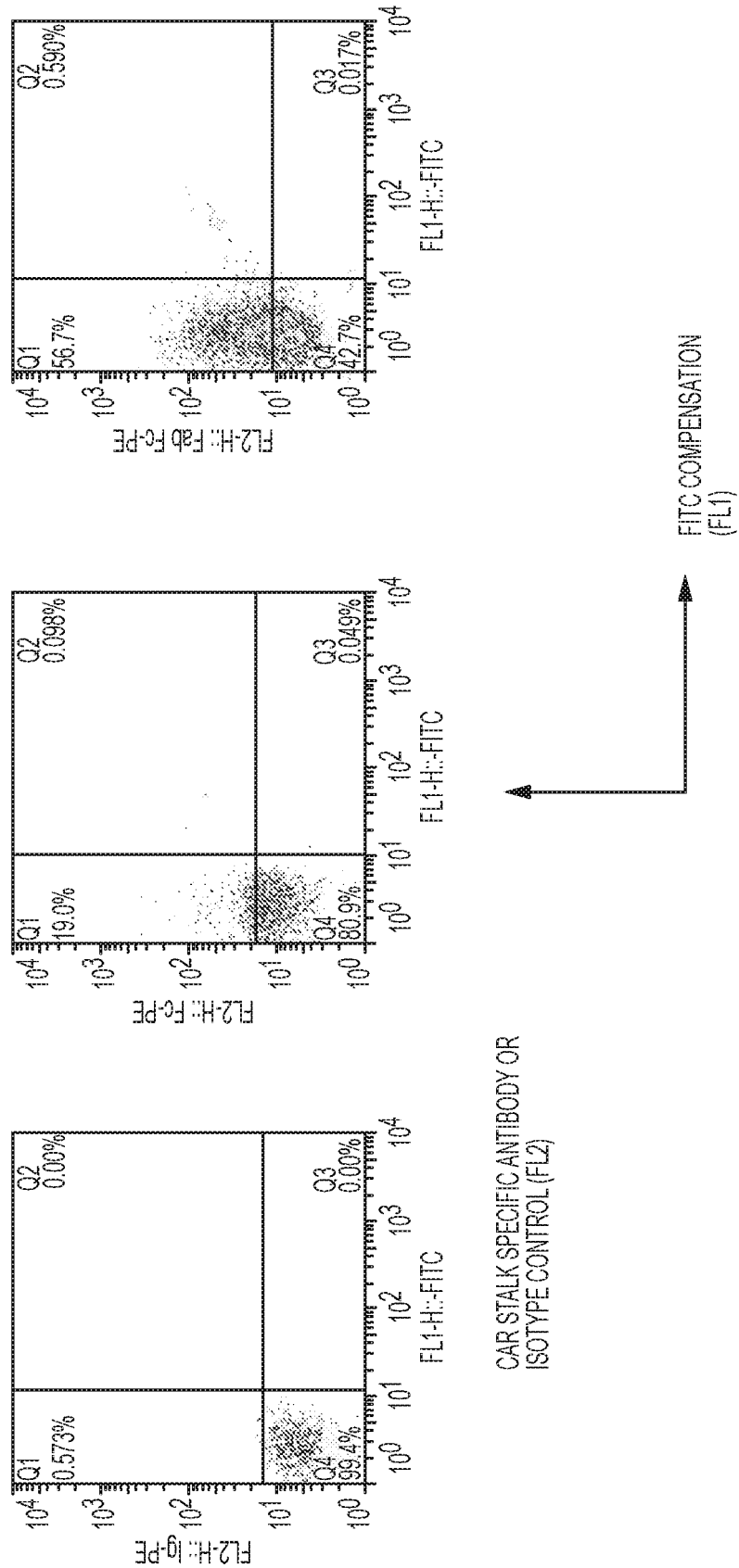

PBMCs were electroporated with DNA encoding for HER1-HER3 CAR (containing either CD28 or CD137 endodomain signaling). The transfection used the Sleeping Beauty-based transposon system (described herein above) to mediate genomic integration of the constructs (see, e.g., International (PCT) Application No. PCT/US14/38005, incorporated herein by reference). Cells were propagated on irradiated AaPc at 1:2 ratio of CAR T cells and universal antigen presenting cells (uAPC; K562$^{Cneg}$ CAR ligand) (see, e.g., International (PCT) Patent Application no. PCT/US14/39365, incorporated herein by reference, which describes uAPCs). The uAPC cells express an antibody that binds to IgG4 hinge region common to many CAR constructs and therefore can stimulate growth of CAR-expressing T-cells without the need for target antigen specific for the given CAR construct. Flow cytometry analysis of the resulting CAR T-cells show an emergence of CAR$^+$ T cells at Day 14 of co-culture with irradiated K562 HLA$^{Cnull}$ expressing a CAR-activating ligand (FIG. 1B).

The kinetics of both HER1-3 CD28z (comprising from N—to C-terminus HER1/HER3-binding scFv-IgG$_4$-CH$_3$—CD28-CD3z; SEQ ID NO: 10) and HER1-3 CD137z (comprising from N—to C-terminus HER1/HER3-binding scFv-IgG$_4$-CH$_3$—CD137-CD3z; SEQ ID NO: 9) CAR-T cell expansion on cultured on K562$^{Cneg}$ uAPC (universal APC) was also assessed. CAR$^+$ T cells are activated signal via stalk of the CAR only in absence of T-cell co-stimulation. The proliferation of CAR+T cells was sub-optimal in absence of antigen and with minimal stimulation from APC. HER1-3 CD137z CAR$^+$T cells showed better proliferation and survival on universal APC as compared to CAR-T cells containing CD28 signaling domain (FIGS. 2A-B).

Example 2

Figure 3A:
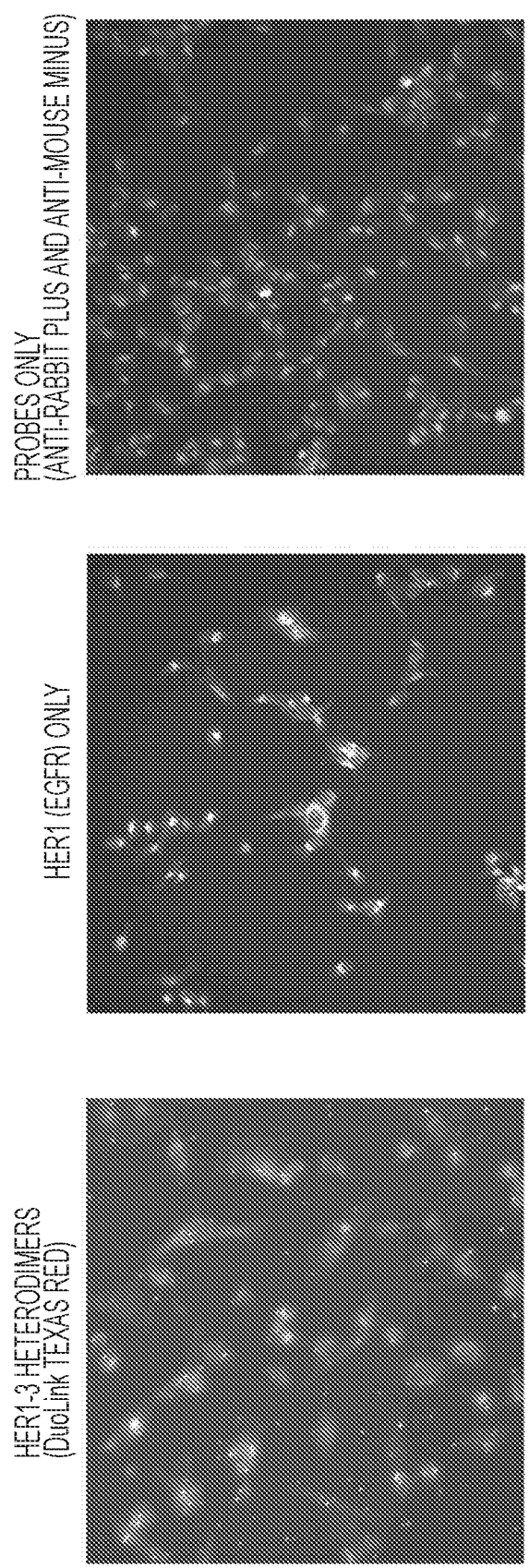

Detection of HER1-3 Heterodimer in Breast Cancer Tumor Cells by In Situ Proximity Ligation Assay To detect HER1 and HER3 heterodimer two separate primary antibodies against HER1 and HER3 (Biolegend)

were used along with proximity ligation assay (PLA) probes and reagents for in situ polymerase reaction (Sigma). Antibodies were titrated previously to reduce background noise. For control purposes, cells were treated with either single antibody or PLA probes only control (anti-rabbit Plus and anti-mouse Minus). Detection was based on signal amplification captured digitally via fluorescence microscope (Leica DMI 6000). Images were analyzed by Metamorph™ imaging system. The results for HER1/HER3 positive MDA-MB-231 breast cancer tumor cells are shown in FIGS. 3A-B, and the results for SK-Br3 and MCF7 are shown in FIG. 3C. HER1-3 heterodimer signals are marked as precise dots on cell surface. Results show that MDA-MB-231 appeared to have the highest amount of HER1/HER3 heterodimers.

Example 3

EGFR Expression and Functionality in a Model MDA-MB-231 BC Tumor Line

Figure 4A:
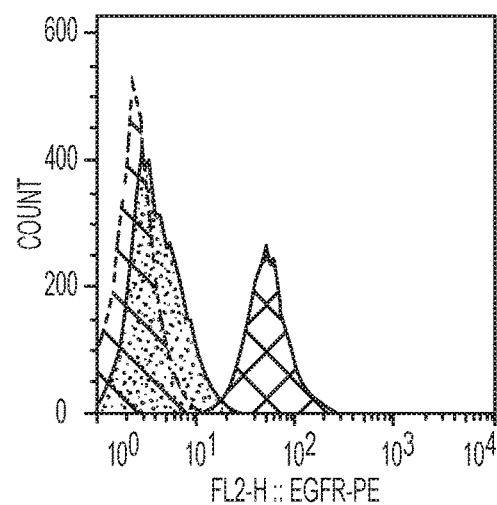
FIGS. 4A-4B—EGFR expression and functionality in a model MDA-MB-231 BC tumor line. EGFR was knocked out at genomic level in the MDA-MB-231 cells by genome editing tool (CRISPR-Cas9). Cells were then assessed for EGFR expression by flow cytometry. (A) Flow cytometry analysis show histograms representing MDA-MB-231 cells only as background control/no primary antibody (dotted line; far left peak), wild type MDA-MB-231 cells (far right peak) and MDA-MB-231 EGFR$^{-null}$ knock out cells (center peak) stained with anti-EGFR antibody (BD). (B) Dot plot analysis confirms down-regulation of EGFR in the knock-out cells.
Figure 4B:
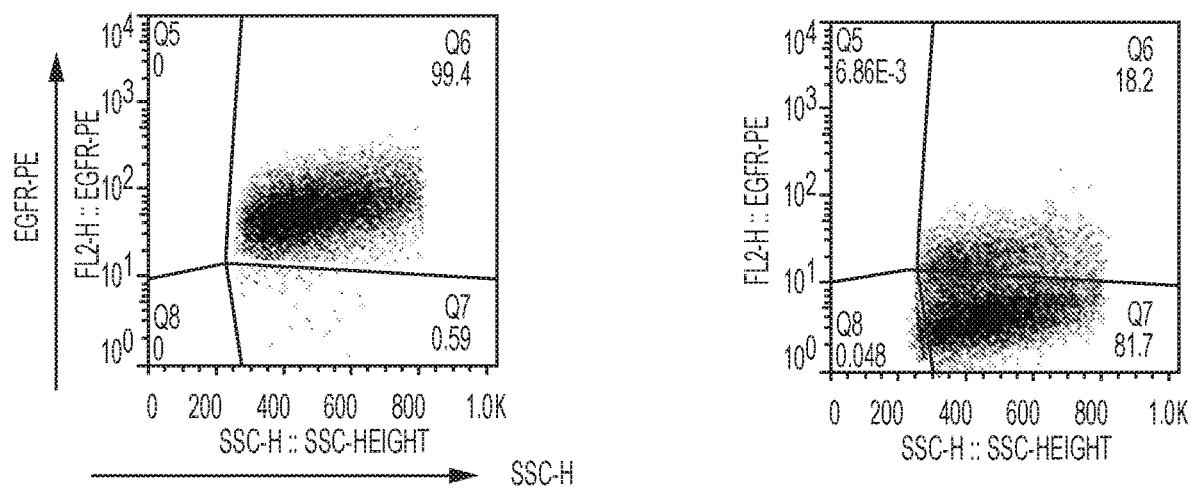

EGFR (HER1) from MB-231 cell line was knocked out at genomic level by using a CRISPR-Cas9 based genome editing tool. Both upper and lower strand oligonucleotide guided RNA (gRNA) specific to Exon 1 and Exon 9 of EGFR (HER1) gene loci were synthesized de novo. Oligonucleotide pairs were annealed as gRNA template and then cloned into plasmid (pX459-U6) backbone bearing CRISPR-Cas9 protein sequences. After transformation plasmids were purified from competent cells and sequence verified. DNA encoding CRISPR-Cas9 EGFR-E1 or E9 were electroporated into MDA-MB-231 cells by a 4D nucleofector electroporator as per manufacturer's instruction (program CH-125). $EGFR^{KO}$ cells were selected on puromycin drug (1 μg/mL) in culture. Expression was verified by flow cytometry using EGFR specific antibody (Biolegend) (FIGS. 4A-4B).

Three different EGFR loci (Exon 1, 8 and 9) were targeted for gene specific knockout of EGFR (HER1) from MB-231 cell line using CRISPR-Cas9 system. Exon 1 targeting guided RNA worked efficiently in knocking out EGFR gene from MB-231 which abrogated surface expression by 70%. After 3 weeks of selection in puro-drug a very low percentage of cells retained EGFR expression which could be due to emergence of escape variants or because of cells that might have developed drug resistance. $EGFR^{KO}$ MB-231 cells grew slower with cell doubling time reduced to $\frac{1}{3}^{rd}$ of that of parental cell line's growth kinetics. No other morphological abnormality was noticed during culture. The results demonstrate that the model cell line may be useful in testing for EGFR-HER3 CAR specificity.

Example 4

Cytolytic Activity of HER1-3 CAR T Cells Against Breast Tumor Cells

Specific cytolytic activity of HER1-3 CAR T cells against breast tumor cells was shown in a short term chromium release assay (CRA). Tumor targets were incubated with $^{51}$Cr as per standard protocol to radio-label cells. Target cells were selected based on EGFR and HER3 expression level, presence of heterodimers were confirmed by Duolink® based proximity ligation assay (see Example 2 above). Specificity of HER1-3 CAR was ascertained through lysis of multiple breast cancer cell lines with evidence of presence or lack of HER1-HER3 heterodimer. Specific lysis was calculated at different effector to target ratio (E:T). Data plots showed different level of killing in various breast cancer tumors that expresses different level of HER1-3 heterodimer (FIG. 5).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

REFERENCES

The following references, to the extent that they provide exemplary procedural or other details supplementary to those set forth herein, are specifically incorporated herein by reference.

U.S. Pat. No. 4,690,915
U.S. Pat. No. 6,225,042
U.S. Pat. No. 6,355,479
U.S. Pat. No. 6,362,001
U.S. Pat. No. 6,410,319
U.S. Pat. No. 6,489,458
U.S. Pat. No. 6,790,662
U.S. Pat. No. 7,109,304
U.S. Pat. No. 7,148,203
U.S. Pat. No. 8,227,432
U.S. Pat. No. 8,906,682
U.S. Patent Application Publication No. 2009/0017000
U.S. Patent Application Publication No. 2009/0004142
U.S. Patent Application Publication No. 2011/0117072
U.S. Patent Application Publication No. 2012/0121596
U.S. Patent Application Publication No. 2013/0280285
U.S. Patent Application Publication No. 2014/0274909
PCT Publication No. WO2007/103009
PCT Publication No. WO/2014/190273
PCT Application No. PCT/US2014/039365
PCT Application No. PCT/US14/39365
PCT Application No. PCT/US14/38005
Altenschmidt et al., *J. Mol. Med.*, 75:259, 1997.
Barthel and Goldfeld, *J. Immunol.*, 171:3612-3619, 2003.
Brentjens et al., *Blood*, 118:4817-4828, 2011.
Brentjens et al., *Sci. Transl. Med.*, 5:177ra138, 2013.
Brocker et al., *Adv. Immunol.*, 68:257, 1998.
Cooper and Bollard, *Blood*, 119:2700-2702, 2012.
Corrigan-Curay et al., *Molecular Therapy.* 22, 1564-1574, 2014.
Eshhar et al., *Proc. Natl. Acad. Sci. U.S.A*, 90:720, 1993.
Eshhar, *Cancer Immunol. Immunother.*, 45:131, 1997.
Fitzer-Attas et al., *J. Immunol.*, 160:145, 1998.
Frauwirth et al., *Immunity*, 16:769-777, 2002.
Gross et al., *FASEB J.*, 6:3370, 1992.
Grupp et al., *New Eng. J. of Med.*, 18:1509-1518, 2013.
Hekele et al., *Int. J. Cancer*, 68:232, 1996.
Hwu et al., *Cancer Res.*, 55:3369, 1995.
Ivics et al., *Cell*, 91(4):501-510, 1997.
Jena et al., *Blood*, 116:1035-1044, 2010.
Jena et al., *Curr. Hematol. Malig. Rep.*, 9:50-56, 2014.
Kalos et al., *Sci. Transl. Med.*, 3:95ra73, 2011.
Kim et al., *Nature*, 22(4):403-410, 2004.
Kochenderfer et al., *Blood*, 116:4099-4102, 2010.
Kochenderfer et al., *Blood*, 119:2709-2720, 2012.

Krauss et al., *Immunity,* 15:497-502, 2001.
Marodon et al., *Blood,* 101:3416-3423, 2003.
Maude et al., *N. Engl. J. Med.,* 371:1507-1517, 2014.
Moritz et al., *Proc. Natl. Acad. Sci. U.S.A,* 91:4318, 1994.
Mates et al., *Nat. Genetics.* 41(6):753-61, 2009.
Pearce et al., *Science,* 342:210, 2013.
Porter et al., *N. Engl. J. Med.,* 365:725-733, 2011.
Remington's Pharmaceutical Sciences, 16th Ed., Mack, ed. (1980)
Roberts et al., *Blood,* 84:2878, 1994.
Rushworth et al., *J. of Immunotherapy.* 37:204-213, 2014.
Schneider, *J. Embryol. Exp. Morph.,* 27:353-365, 1972.
Stancovski et al., *J. Immunol.,* 151:6577, 1993.
Till et al., *Blood,* 112:2261-2271, 2008.
Topalian and Rosenberg, *Acta Haematol.,* 78(Suppl. 1):75-76, 1987.
van der Windt et al., *Immunity,* 36:68-78, 2012.
Weijtens et al., *J. Immunol.,* 157:836, 1996.

The invention claimed is:

1. A nucleic acid molecule encoding a CAR polypeptide, wherein said CAR polypeptide comprises a scFv; a hinge domain; a transmembrane domain(s) and one or more intracellular cell signaling domain, wherein the scFv of said CAR comprises (i) an immunoglobulin light chain variable domain comprising SEQ ID NO. 4 and (ii) immunoglobulin heavy chain variable domain comprising SEQ ID NO: 8.

2. An isolated immune effector cell comprising a nucleic acid of claim 1.

3. A pharmaceutical composition comprising a population of immune effector cells of claim 2 in a pharmaceutically acceptable carrier.

4. The immune effector cell of claim 2, wherein the immune effector cell is a T-cell, a NK cell, a NK T cell or a T-cell progenitor.

5. The immune effector cell of claim 2, further comprising a membrane-bound cytokine.

6. The immune effector cell of claim 5, wherein the membrane-bound cytokine is membrane-bound IL-15.

7. The immune effector cell of claim 2, wherein the immune effector cell is transformed with a viral or a non-viral vector comprising the nucleic acid encoding a CAR polypeptide.

8. The immune effector cell of claim 7, wherein the non-viral vector comprises a Sleeping Beauty transposon/transposase system.

9. A pharmaceutical composition comprising an anti-tumor effective amount of a population of human T cells, said cells comprising a chimeric antigen receptor (CAR) that binds to HER1-HER3 heterodimer protein complex, said CAR comprising (i) an immunoglobulin light chain variable domain comprising SEQ ID NO. 4 and (ii) immunoglobulin heavy chain variable domain comprising SEQ ID NO: 8.

10. A chimeric antigen receptor (CAR) polypeptide comprising a scFv; a hinge domain; a transmembrane domain(s) and one or more intracellular cell signaling domain, wherein the scFv of said CAR comprises (i) an immunoglobulin light chain variable domain comprising SEQ ID NO. 4 and (ii) immunoglobulin heavy chain variable domain comprising SEQ ID NO: 8.

11. The CAR polypeptide of claim 10, wherein the CAR comprises an amino acid sequence at least 90% identical to SEQ ID NO: 9.

12. The CAR polypeptide of claim 10, wherein the CAR comprises an amino acid sequence identical to SEQ ID NO: 9.

13. The CAR polypeptide of claim 10, wherein the CAR comprises an amino acid sequence at least 90% identical to SEQ ID NO: 10.

14. The CAR polypeptide of claim 10, wherein the CAR comprises an amino acid sequence identical to SEQ ID NO: 10.

15. A method of treating a subject with cancer comprising administering an anti-tumor effective amount of chimeric antigen receptor (CAR) T-cells that expresses a CAR polypeptide of claim 10.

16. The method of claim 15, wherein the subject has breast cancer or ovarian cancer.

17. The method of claim 15, wherein the subject has melanoma, non-small cell lung cancer, gastric cancer, colorectal cancer or pancreatic cancer.

18. The method of claim 15, wherein the subject has a cancer that is resistant to trastuzumab or a tyrosine kinase inhibitor therapy.

* * * * *

SEQUENCE LISTING

```
<160> NUMBER OF SEQ ID NOS: 21

<210> SEQ ID NO 1
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 1

Asn Ile Ala Thr Asp Val
1               5

<210> SEQ ID NO 2
<211> LENGTH: 4
<212> TYPE: PRT
<213> ORGANISM: Artificial sequence
<220> FEATURE:
<223> OTHER INFORMATION: Synthetic polypeptide

<400> SEQUENCE: 2

Ser Ala Ser Phe
1

<210> SEQ ID NO 3
<211> LENGTH: 6
<212> TYPE: PRT
<213> ORGANISM: Artificial sequence
<220> FEATURE:
<223> OTHER INFORMATION: Synthetic polypeptide

<400> SEQUENCE: 3

Ser Glu Pro Glu Pro Tyr
1               5

<210> SEQ ID NO 4
<211> LENGTH: 112
<212> TYPE: PRT
<213> ORGANISM: Artificial sequence
<220> FEATURE:
<223> OTHER INFORMATION: Synthetic polypeptide

<400> SEQUENCE: 4

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ser Thr Ala Val Ala Trp Ile Gln Gln Lys Pro Gly Lys Ala Pro
        35                  40                  45

Lys Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80
```

```
Ser Leu Gln Pro Glu Asp Phe Ala Thr Tyr Tyr Cys Gln Gln Ser Glu
                85                  90                  95

Pro Glu Pro Tyr Thr Phe Gly Gln Gly Thr Lys Val Glu Ile Lys Arg
            100                 105                 110

<210> SEQ ID NO 5
<211> LENGTH: 5
<212> TYPE: PRT
<213> ORGANISM: Artificial sequence
<220> FEATURE:
<223> OTHER INFORMATION: Synthetic polypeptide

<400> SEQUENCE: 5

Leu Ser Gly Asp Trp
1               5

<210> SEQ ID NO 6
<211> LENGTH: 10
<212> TYPE: PRT
<213> ORGANISM: Artificial sequence
<220> FEATURE:
<223> OTHER INFORMATION: Synthetic polypeptide

<400> SEQUENCE: 6

Glu Ile Ser Ala Ala Gly Gly Tyr Thr Asp
1               5                   10

<210> SEQ ID NO 7
<211> LENGTH: 12
<212> TYPE: PRT
<213> ORGANISM: Artificial sequence
<220> FEATURE:
<223> OTHER INFORMATION: Synthetic polypeptide

<400> SEQUENCE: 7

Glu Ser Arg Val Ser Phe Glu Ala Ala Met Asp Tyr
1               5                   10

<210> SEQ ID NO 8
<211> LENGTH: 118
<212> TYPE: PRT
<213> ORGANISM: Artificial sequence
<220> FEATURE:
<223> OTHER INFORMATION: Synthetic polypeptide

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Leu Ser Gly Asp
            20                  25                  30

Trp Val Ile His Trp Val Arg Gln Ala Pro Gly Lys Gly Leu Glu Trp
        35                  40                  45

Val Gly Glu Ile Ser Ala Ala Gly Gly Tyr Thr Asp Tyr Ala Asp Ser
    50                  55                  60

Val Lys Gly Arg Phe Thr Ile Ser Ala Asp Thr Ser Lys Asn Thr Ala
65                  70                  75                  80

Tyr Leu Gln Met Asn Ser Leu Arg Ala Glu Asp Thr Ala Val Tyr Tyr
                85                  90                  95

Cys Ala Arg Glu Ser Arg Val Ser Phe Glu Ala Ala Met Asp Tyr Trp
            100                 105                 110

Gly Gln Gly Thr Leu Val
            115
```

```
<210> SEQ ID NO 9
<211> LENGTH: 500
<212> TYPE: PRT
<213> ORGANISM: Artificial sequence
<220> FEATURE:
<223> OTHER INFORMATION: Synthetic polypeptide

<400> SEQUENCE: 9
```

| | | | | | | | | | | | | | | |
|---|---|---|---|---|---|---|---|---|---|---|---|---|---|---|
| Asp | Ile | Gln | Met | Thr | Gln | Ser | Pro | Ser | Ser | Leu | Ser | Ala | Ser | Val | Gly |
| 1 | | | | 5 | | | | | 10 | | | | | 15 | |

| Asp | Arg | Val | Thr | Ile | Thr | Cys | Arg | Ala | Ser | Gln | Asn | Ile | Ala | Thr | Asp |
|---|---|---|---|---|---|---|---|---|---|---|---|---|---|---|---|
| | | | 20 | | | | | 25 | | | | | 30 | | |

| Val | Ser | Thr | Ala | Val | Ala | Trp | Ile | Gln | Gln | Lys | Pro | Gly | Lys | Ala | Pro |
|---|---|---|---|---|---|---|---|---|---|---|---|---|---|---|---|
| | | 35 | | | | | 40 | | | | | 45 | | | |

| Lys | Leu | Leu | Ile | Tyr | Ser | Ala | Ser | Phe | Leu | Tyr | Ser | Gly | Val | Pro | Ser |
|---|---|---|---|---|---|---|---|---|---|---|---|---|---|---|---|
| 50 | | | | | 55 | | | | | 60 | | | | | |

| Arg | Phe | Ser | Gly | Ser | Gly | Ser | Gly | Thr | Asp | Phe | Thr | Leu | Thr | Ile | Ser |
|---|---|---|---|---|---|---|---|---|---|---|---|---|---|---|---|
| 65 | | | | | 70 | | | | | 75 | | | | | 80 |

| Ser | Leu | Gln | Pro | Glu | Asp | Phe | Ala | Thr | Tyr | Tyr | Cys | Gln | Gln | Ser | Glu |
|---|---|---|---|---|---|---|---|---|---|---|---|---|---|---|---|
| | | | | 85 | | | | | 90 | | | | | 95 | |

| Pro | Glu | Pro | Tyr | Thr | Phe | Gly | Gln | Gly | Thr | Lys | Val | Glu | Ile | Lys | Arg |
|---|---|---|---|---|---|---|---|---|---|---|---|---|---|---|---|
| | | | 100 | | | | | 105 | | | | | 110 | | |

| Gly | Ser | Thr | Ser | Gly | Ser | Gly | Lys | Pro | Gly | Ser | Gly | Glu | Gly | Ser | Thr |
|---|---|---|---|---|---|---|---|---|---|---|---|---|---|---|---|
| | | 115 | | | | | 120 | | | | | 125 | | | |

| Lys | Gly | Glu | Val | Gln | Leu | Val | Glu | Ser | Gly | Gly | Gly | Leu | Val | Gln | Pro |
|---|---|---|---|---|---|---|---|---|---|---|---|---|---|---|---|
| | 130 | | | | | 135 | | | | | 140 | | | | |

| Gly | Gly | Ser | Leu | Arg | Leu | Ser | Cys | Ala | Ala | Ser | Gly | Phe | Thr | Leu | Ser |
|---|---|---|---|---|---|---|---|---|---|---|---|---|---|---|---|
| 145 | | | | | 150 | | | | | 155 | | | | | 160 |

| Gly | Asp | Trp | Val | Ile | His | Trp | Val | Arg | Gln | Ala | Pro | Gly | Lys | Gly | Leu |
|---|---|---|---|---|---|---|---|---|---|---|---|---|---|---|---|
| | | | | 165 | | | | | 170 | | | | | 175 | |

| Glu | Trp | Val | Gly | Glu | Ile | Ser | Ala | Ala | Gly | Gly | Tyr | Thr | Asp | Tyr | Ala |
|---|---|---|---|---|---|---|---|---|---|---|---|---|---|---|---|
| | | | 180 | | | | | 185 | | | | | 190 | | |

| Asp | Ser | Val | Lys | Gly | Arg | Phe | Thr | Ile | Ser | Ala | Asp | Thr | Ser | Lys | Asn |
|---|---|---|---|---|---|---|---|---|---|---|---|---|---|---|---|
| | | 195 | | | | | 200 | | | | | 205 | | | |

| Thr | Ala | Tyr | Leu | Gln | Met | Asn | Ser | Leu | Arg | Ala | Glu | Asp | Thr | Ala | Val |
|---|---|---|---|---|---|---|---|---|---|---|---|---|---|---|---|
| | 210 | | | | | 215 | | | | | 220 | | | | |

| Tyr | Tyr | Cys | Ala | Arg | Glu | Ser | Arg | Val | Ser | Phe | Glu | Ala | Ala | Met | Asp |
|---|---|---|---|---|---|---|---|---|---|---|---|---|---|---|---|
| 225 | | | | | 230 | | | | | 235 | | | | | 240 |

| Tyr | Trp | Gly | Gln | Gly | Thr | Leu | Val | Pro | Ser | Asp | Ile | Ala | Val | Glu | Trp |
|---|---|---|---|---|---|---|---|---|---|---|---|---|---|---|---|
| | | | | 245 | | | | | 250 | | | | | 255 | |

| Glu | Ser | Asn | Gly | Gln | Pro | Glu | Asn | Asn | Tyr | Lys | Thr | Thr | Pro | Pro | Val |
|---|---|---|---|---|---|---|---|---|---|---|---|---|---|---|---|
| | | | 260 | | | | | 265 | | | | | 270 | | |

| Leu | Asp | Ser | Asp | Gly | Ser | Phe | Phe | Leu | Tyr | Ser | Arg | Leu | Thr | Val | Asp |
|---|---|---|---|---|---|---|---|---|---|---|---|---|---|---|---|
| | | 275 | | | | | 280 | | | | | 285 | | | |

| Lys | Ser | Arg | Trp | Gln | Glu | Gly | Asn | Val | Phe | Ser | Cys | Ser | Val | Met | His |
|---|---|---|---|---|---|---|---|---|---|---|---|---|---|---|---|
| | 290 | | | | | 295 | | | | | 300 | | | | |

| Glu | Ala | Leu | His | Asn | His | Tyr | Thr | Gln | Lys | Ser | Leu | Ser | Leu | Ser | Leu |
|---|---|---|---|---|---|---|---|---|---|---|---|---|---|---|---|
| 305 | | | | | 310 | | | | | 315 | | | | | 320 |

| Gly | Lys | Trp | Val | Leu | Val | Val | Val | Gly | Gly | Val | Leu | Ala | Cys | Tyr | Ser |
|---|---|---|---|---|---|---|---|---|---|---|---|---|---|---|---|
| | | | | 325 | | | | | 330 | | | | | 335 | |

| Leu | Leu | Val | Thr | Val | Ala | Phe | Ile | Ile | Lys | Arg | Gly | Arg | Lys | Lys | Leu |
|---|---|---|---|---|---|---|---|---|---|---|---|---|---|---|---|
| | | | 340 | | | | | 345 | | | | | 350 | | |

| Leu | Tyr | Ile | Phe | Lys | Gln | Pro | Phe | Met | Arg | Pro | Val | Gln | Thr | Thr | Gln |
|---|---|---|---|---|---|---|---|---|---|---|---|---|---|---|---|
| | | 355 | | | | | 360 | | | | | 365 | | | |

```
Glu Glu Asp Gly Cys Ser Cys Arg Phe Pro Glu Glu Gly Gly
    370                 375                 380

Cys Glu Leu Arg Val Lys Phe Ser Arg Ser Ala Asp Ala Pro Ala Tyr
385                 390                 395                 400

Gln Gln Gly Gln Asn Gln Leu Tyr Asn Glu Leu Asn Leu Gly Arg Arg
                405                 410                 415

Glu Glu Tyr Asp Val Leu Asp Lys Arg Arg Gly Arg Asp Pro Glu Met
            420                 425                 430

Gly Gly Lys Pro Gln Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg
            500

<210> SEQ ID NO 10
<211> LENGTH: 503
<212> TYPE: PRT
<213> ORGANISM: Artificial sequence
<220> FEATURE:
<223> OTHER INFORMATION: Synthetic polypeptide

<400> SEQUENCE: 10

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asn Ile Ala Thr Asp
            20                  25                  30

Val Ser Thr Ala Val Ala Trp Ile Gln Gln Lys Pro Gly Lys Ala Pro
        35                  40                  45

Lys Leu Leu Ile Tyr Ser Ala Ser Phe Leu Tyr Ser Gly Val Pro Ser
    50                  55                  60

Arg Phe Ser Gly Ser Gly Ser Gly Thr Asp Phe Thr Leu Thr Ile Ser
65                  70                  75                  80

Ser Leu Gln Pro Glu Asp Phe Ala Thr Tyr Tyr Cys Gln Gln Ser Glu
                85                  90                  95

Pro Glu Pro Tyr Thr Phe Gly Gln Gly Thr Lys Val Glu Ile Lys Arg
            100                 105                 110

Gly Ser Thr Ser Gly Ser Gly Lys Pro Gly Ser Gly Glu Gly Ser Thr
        115                 120                 125

Lys Gly Glu Val Gln Leu Val Glu Ser Gly Gly Gly Leu Val Gln Pro
    130                 135                 140

Gly Gly Ser Leu Arg Leu Ser Cys Ala Ala Ser Gly Phe Thr Leu Ser
145                 150                 155                 160

Gly Asp Trp Val Ile His Trp Val Arg Gln Ala Pro Gly Lys Gly Leu
                165                 170                 175

Glu Trp Val Gly Glu Ile Ser Ala Ala Gly Gly Tyr Thr Asp Tyr Ala
            180                 185                 190

Asp Ser Val Lys Gly Arg Phe Thr Ile Ser Ala Asp Thr Ser Lys Asn
        195                 200                 205
```

```
Thr Ala Tyr Leu Gln Met Asn Ser Leu Arg Ala Glu Asp Thr Ala Val
        210                 215                 220
Tyr Tyr Cys Ala Arg Glu Ser Arg Val Ser Phe Glu Ala Ala Met Asp
225                 230                 235                 240
Tyr Trp Gly Gln Gly Thr Leu Val Pro Ser Asp Ile Ala Val Glu Trp
                    245                 250                 255
Glu Ser Asn Gly Gln Pro Glu Asn Asn Tyr Lys Thr Thr Pro Pro Val
                260                 265                 270
Leu Asp Ser Asp Gly Ser Phe Phe Leu Tyr Ser Arg Leu Thr Val Asp
            275                 280                 285
Lys Ser Arg Trp Gln Glu Gly Asn Val Phe Ser Cys Ser Val Met His
290                 295                 300
Glu Ala Leu His Asn His Tyr Thr Gln Lys Ser Leu Ser Leu Ser Leu
305                 310                 315                 320
Gly Lys Phe Trp Val Leu Val Val Gly Gly Val Leu Ala Cys Tyr
                    325                 330                 335
Ser Leu Leu Val Thr Val Ala Phe Ile Ile Phe Trp Val Arg Ser Lys
                340                 345                 350
Arg Ser Arg Leu Leu His Ser Asp Tyr Met Asn Met Thr Pro Arg Arg
            355                 360                 365
Pro Gly Pro Thr Arg Lys His Tyr Gln Pro Tyr Ala Pro Pro Arg Asp
370                 375                 380
Phe Ala Ala Tyr Arg Ser Arg Val Lys Phe Ser Arg Ser Ala Asp Ala
385                 390                 395                 400
Pro Ala Tyr Gln Gln Gly Gln Asn Gln Leu Tyr Asn Glu Leu Asn Leu
                    405                 410                 415
Gly Arg Arg Glu Glu Tyr Asp Val Leu Asp Lys Arg Arg Gly Arg Asp
                420                 425                 430
Pro Glu Met Gly Gly Lys Pro Gln Arg Arg Lys Asn Pro Gln Glu Gly
            435                 440                 445
Leu Tyr Asn Glu Leu Gln Lys Asp Lys Met Ala Glu Ala Tyr Ser Glu
450                 455                 460
Ile Gly Met Lys Gly Glu Arg Arg Arg Gly Lys Gly His Asp Gly Leu
465                 470                 475                 480
Tyr Gln Gly Leu Ser Thr Ala Thr Lys Asp Thr Tyr Asp Ala Leu His
                485                 490                 495
Met Gln Ala Leu Pro Pro Arg
            500

<210> SEQ ID NO 11
<211> LENGTH: 32
<212> TYPE: PRT
<213> ORGANISM: Homo sapiens

<400> SEQUENCE: 11

Phe Ala Cys Asp Ile Tyr Ile Trp Ala Pro Leu Ala Gly Thr Cys Gly
1               5                   10                  15
Val Leu Leu Leu Ser Leu Val Ile Thr Leu Tyr Cys Asn His Arg Asn
            20                  25                  30

<210> SEQ ID NO 12
<211> LENGTH: 27
<212> TYPE: PRT
<213> ORGANISM: Homo sapiens
```

<400> SEQUENCE: 12

Phe Trp Val Leu Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 13
<211> LENGTH: 112
<212> TYPE: PRT
<213> ORGANISM: Homo sapiens

<400> SEQUENCE: 13

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 14
<211> LENGTH: 41
<212> TYPE: PRT
<213> ORGANISM: Homo sapiens

<400> SEQUENCE: 14

Arg Ser Lys Arg Ser Arg Gly Gly His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 15
<211> LENGTH: 42
<212> TYPE: PRT
<213> ORGANISM: Homo sapiens

<400> SEQUENCE: 15

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 16
<211> LENGTH: 230
<212> TYPE: PRT
<213> ORGANISM: Homo sapiens

<400> SEQUENCE: 16

Glu Ser Lys Tyr Gly Pro Pro Cys Pro Pro Cys Pro Ala Pro Glu Phe
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys Met
225                 230

<210> SEQ ID NO 17
<211> LENGTH: 230
<212> TYPE: PRT
<213> ORGANISM: Artificial Sequence
<220> FEATURE:
<223> OTHER INFORMATION: Mutant IgG4-Fc

<400> SEQUENCE: 17

Glu Ser Lys Tyr Gly Pro Pro Cys Pro Pro Cys Pro Ala Pro Glu Phe
1               5                   10                  15

Glu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser Gln Glu Asp Pro Glu Val Gln Phe Asn Trp Tyr Val Asp Gly Val
    50                  55                  60

Glu Val His Asn Ala Lys Thr Lys Pro Arg Glu Glu Gln Phe Gln Ser
65                  70                  75                  80

Thr Tyr Arg Val Val Ser Val Leu Thr Val Leu His Gln Asp Trp Leu
                85                  90                  95

```
Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
        115                 120                 125

Gln Val Tyr Thr Leu Pro Pro Ser Gln Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
210                 215                 220

Leu Ser Leu Gly Lys Met
225                 230

<210> SEQ ID NO 18
<211> LENGTH: 43
<212> TYPE: PRT
<213> ORGANISM: Homo sapiens

<400> SEQUENCE: 18

Lys Pro Thr Thr Thr Pro Ala Pro Arg Pro Pro Thr Pro Ala Pro Thr
1               5                   10                  15

Ile Ala Ser Gln Pro Leu Ser Leu Arg Pro Glu Ala Cys Arg Pro Ala
            20                  25                  30

Ala Gly Gly Ala Val His Thr Arg Gly Leu Asp
        35                  40

<210> SEQ ID NO 19
<211> LENGTH: 12
<212> TYPE: PRT
<213> ORGANISM: Artificial Sequence
<220> FEATURE:
<223> OTHER INFORMATION: Synthetic hinge

<400> SEQUENCE: 19

Glu Ser Lys Tyr Gly Pro Pro Cys Pro Pro Cys Pro
1               5                   10

<210> SEQ ID NO 20
<211> LENGTH: 18
<212> TYPE: PRT
<213> ORGANISM: Artificial Sequence
<220> FEATURE:
<223> OTHER INFORMATION: Synthetic linker

<400> SEQUENCE: 20

Gly Ser Thr Ser Gly Ser Gly Lys Pro Gly Ser Gly Glu Gly Ser Thr
1               5                   10                  15

Lys Gly

<210> SEQ ID NO 21
<211> LENGTH: 22
<212> TYPE: PRT
<213> ORGANISM: Homo sapiens
```

```
<400> SEQUENCE: 21

Met Leu Leu Leu Val Thr Ser Leu Leu Leu Cys Glu Leu Pro His Pro
1               5                   10                  15

Ala Phe Leu Leu Ile Pro
            20
```